United States Patent [19]

Hartung et al.

[11] Patent Number: 5,260,461

[45] Date of Patent: * Nov. 9, 1993

[54] LIGANDS FOR ADH: CINCHONA ALKALOIDS AND MODERATELY SIZED ORGANIC SUBSTITUENTS LINKED THROUGH A PLANAR AROMATIC SPACER GROUP

[75] Inventors: Jens Hartung, Rodgau-Weiskirchen, Fed. Rep. of Germany; K. Barry Sharpless, La Jolla, Calif.

[73] Assignee: Massachusetts Institute of Technology, Cambridge, Mass.

[ * ] Notice: The portion of the term of this patent subsequent to Oct. 23, 2007 has been disclaimed.

[21] Appl. No.: 775,683

[22] Filed: Oct. 10, 1991

Related U.S. Application Data

[63] Continuation-in-part of Ser. No. 699,183, May 13, 1991, which is a continuation of Ser. No. 2,778, Apr. 23, 1991, which is a continuation-in-part of Ser. No. 512,934, Apr. 23, 1990, Pat. No. 5,126,494, which is a continuation-in-part of Ser. No. 250,378, Sep. 28, 1988, Pat. No. 4,965,364, which is a continuation-in-part of Ser. No. 159,068, Feb. 23, 1988, Pat. No. 4,871,855, which is a continuation-in-part of Ser. No. 142,692, Nov. 11, 1988, abandoned.

[51] Int. Cl.$^5$ .................. C07C 215/34; C07C 33/26; C07C 29/48; C07C 31/20; C07C 69/734; C07C 69/735; C07C 33/02; C07C 33/26; C07D 453/02; C07D 453/04; C07D 67/313

[52] U.S. Cl. .................. 549/447; 544/237; 544/238; 546/133; 546/134; 546/135; 549/555; 556/482; 556/489; 560/38; 560/63; 560/104; 560/105; 560/129; 562/129; 564/355; 564/373; 568/806; 568/811; 568/822; 568/852; 568/860

[58] Field of Search ............... 544/237, 238; 546/133, 546/134, 135; 568/860, 807, 715, 833, 847, 852, 806, 811, 822; 564/355, 373; 560/38, 63, 104, 105, 126, 129; 549/447, 555; 562/452

[56] References Cited

U.S. PATENT DOCUMENTS

| | | | |
|---|---|---|---|
| 3,557,117 | 1/1971 | Shetty | 546/134 X |
| 3,792,053 | 2/1974 | Potoski et al. | 546/134 X |
| 3,813,384 | 5/1974 | Vogelsang et al. | 546/134 X |
| 3,869,462 | 3/1975 | Gutzwiller et al. | 546/134 |
| 4,482,763 | 11/1984 | Austin et al. | 568/860 |
| 4,496,778 | 1/1985 | Myers et al. | 568/860 |
| 4,496,779 | 1/1985 | Myers et al. | 568/860 |
| 4,871,855 | 10/1989 | Marko et al. | 546/134 |
| 4,965,364 | 10/1990 | Marko et al. | 546/134 |
| 5,126,494 | 6/1992 | Gilheany et al. | 568/807 |

FOREIGN PATENT DOCUMENTS

| | | | |
|---|---|---|---|
| 0053023 | 6/1982 | European Pat. Off. | 568/860 |
| 0077202 | 4/1983 | European Pat. Off. | 568/860 |
| 0098701 | 1/1984 | European Pat. Off. | 568/860 |
| WO89/02428 | 7/1988 | PCT Int'l Appl. | 568/860 |
| WO89/06225 | 7/1989 | PCT Int'l Appl. | 568/860 |
| WO91/16322 | 10/1991 | PCT Int'l Appl. | 568/807 |

OTHER PUBLICATIONS

K. B. Sharpless et al., *J. of Org. Chem.*, 56(15): 4585-4588, "New Ligands Double the Scope of the Catalytic Asymmetric Dihydroxylation of Olefins", (Jul. 19, 1991).

B. Bushan Lohray et al., *Tetrahedron Letters*, 30(16): 2041-2044, "Documenting the Scope of the Catalytic Asymmetric Dihydroxylation" (1989).

(List continued on next page.)

*Primary Examiner*—Floyd D. Higel
*Attorney, Agent, or Firm*—Hamilton, Brook, Smith & Reynolds

[57] ABSTRACT

Osmium-catalyzed methods of addition to an olefin are discussed. In the method of asymmetric dihydroxylation of the present invention, an olefin, a chiral ligand, an organic solvent, an aqueous solution, a base, a ferricyanide salt and an osmium-containing compound are combined. The chiral ligand is an alkaloid or alkaloid derivative linked to an organic substituent of at least 300 daltons molecular weight through a planar aromatic spacer group. The organic substituent can be another alkaloid or alkaloid derivative. With the described chiral ligands, asymmetric dihydroxylation of olefins with high yields and enantiomeric excesses are achieved.

9 Claims, 4 Drawing Sheets

OTHER PUBLICATIONS

Kyu-Sung Jeong et al., *Tetrahedron Letters*, 33(27): 3833-3836, "Asymmetric Dihydroxylation of Enzymes" (Jun. 39, 1992).

Daqiang Xu et al., *J. of Am. Chem. Soc.*, 114:7570-7571 "Selective Asymmetric Dihydroxylation of Dienes" (Sep. 9, 1992).

K. B. Sharpless et al., *J. of Org. Chem.*, 57(10): 2768-2771 "The Osmium-Catalyzed Asymmetric Dihydroxylation: A New Ligand Class and A Process Improvement" (May 8, 1992).

E. N. Jacobsen et al., *J. American Chemical Society*, 110:1968-1970 (1988).

K. B. Sharpless and K. Akashi, *J. American Chemical Society*, 98(7):1986-1987 (1976).

K. Akashi et al., *J. Organic Chemistry*, 43(10): 2063-2066 (1978).

E. Herranz and K. B. Sharpless, I *J. Organic Chemistry*, 43(12): 2544-2548 (1978).

B. A. Cartwright et al., *J.C.S. Chem. Comm.*, pp. 853-854 (1978).

R. Collin et al., *Biochimica et Biophysica Acta*, 354:152-154 (1974).

V. Van Rheenen et al., *Tetrahedron Letters*, 23:1973-1976 (1976).

R. Ray and D. S. Matteson, *Tetrahedron Letters*, 21:449-450 (1980).

S. G. Hentges and K. B. Sharpless, *J. American Chemical Society*, 102(12):4263-4265 (1980).

H. S. Mosher and J. D. Morrison, *Science*, 221:1013-1019 (1983).

T. H. Maugh, *Science*, 221:351-354 (1983).

R. Criegee, *J. Liebigs. Ann. Chem.*, 522:75-96 (1936)—(-Translation from German).

N. Iwasawa et al., *Chemistry Letters*, pp. 1721-1724 (1988).

K. B. Sharpless et al II *J. American Chemical Soc.*, 97:2305-2307 (1975).

K. B. Sharpless et al., III *J. Organic Chemistry*, 41;177-179 (1975).

A. O. Chong et al., *J. Am. Chem. Soc.*, 99:3420-3426 (1977).

E. Herranz et al., II *J. Am. Chem. Soc.*, 100:3596-3598 (1978).

M. Schroder, *Chem. Rev.*, 80:187-213 (1980).

T. Yamada and K. Narasaka, *Chem. Letters*, 131-134 (1986).

K. B. Sharpless, IV *Chemistry in Britain* (Jan. 1986).

M. Tokles and J. K. Snyder, *Tetrahedron Letters*, 27:3951-3954 (1986).

Y. Gao et al., *J. Am. Chem. Soc*, 109:5765-5779 (1987).

Ab. A. Smaardijk and H. Wynberg, *J. Org. Chem.*, 52:135-137 (1987).

K. Tomioka et al., *J. Am. Chem. Soc.*, 109:6213-6215 (1987).

G. Cainelli et al., *Synthesis*, pp. 45-58 (1989).

P. Salvadori et al., *Tetrahedron*, 43(21): 4969-4978 (1987).

M. Inagaki et al., *Bull. Chem. Soc. Jpn.*, 60:4121-4126 (1987).

N. Kobayashi and K. Iwai, I *J. Am. Chem. Soc.*, 100(22):7071-7072 (1978).

P. Hodge et al., I *J. Chem. Soc. Perkin Trans. I*, pp. 2205-2209 (1983).

P. Hodge et al., III *J. Chem. Soc. Perkin Trans. I*, pp. 2327-2231 (1985).

N. Kobayashi and K. Iwai, III *Macromolecules*, 13:31-34 (1980).

K. Hermann and H. Wynberg, *Helvetica Chim. Acta*, 60:2208-2212 (1977).

N. Kobayashi and K. Iwai, IV *J. Polymer Sci., Polymer Chem. Ed.*, 18: 223-233 (1980).

K. Yamauchi et al., I *Bull. Chem. Soc. Jpn.*, 44:3186-3187 (1971).

K. Yamauchi et al., II *J. Macromol. Sci—Chem.*, A10(6):981-991 (1976).

T. Yamashita et al., *Bull. Chem. Soc. Jpn.*, 51(4):1183-1185 (1978).

N. Kobayashi and K. Iwai, V *Tetrahedron Lett.*, 21:2167-2170 (1980).

N. Kobayashi and K. Iwai, VI *J. Polymer Sci., Polym. Lett. Ed.*, 18(6): 417-420 (1980).

N. Kobayashi and K. Iwai, VII *J. Polym. Sci., Polym. Lett. Ed.*, 20(2): 85-90 (1982).

N. Kobayashi and K. Iwai, VIII *Polymer Journal*, 13(3):263-271 (1981).

N. Kobayashi and K. Iwai, IX *J. Polym. Sci., Polym. Chem. Ed.*, 18(3): 923-932 (1980).

Shibata, et al., *Tetrahedron Letters* 31(27), 3817-3820, 1990.

Kwong et al., *Tetrahedron Letters* 31(21), 2999-3002, 1990.

Kim, et al., *Tetrahedron Letters* 31(21), 3003-3006, 1990.

Minato et al., *J. Org. Chem.* 55, 766-768, 1990.

ND THROUGH A PLANAR
LIGANDS FOR ADH: CINCHONA ALKALOIDS AND MODERATELY SIZED ORGANIC SUBSTITUENTS LINKED THROUGH A PLANAR AROMATIC SPACER GROUP

RELATED APPLICATIONS

This is a continuation-in-part (CIP) of U.S. Ser. No. 07/699,183 filed May 13, 1991, which is a continuation in part of application Ser. No. 002,778 filed 23 Apr. 1991, which is a continuation in part of U.S. Ser. No. 07/512,934 filed Apr. 23, 1990, now U.S. Pat. No. 5,126,494 issued Jun. 30, 1992, which is a continuation in part of U.S. Ser. No. 07/250,378 filed Sep. 28, 1988, now U.S. Pat. No. 4,965,364, which is a continuation in part of U.S. Ser. No. 07/159,068, filed Feb. 23, 1988, now U.S. Pat. No. 4,871,855, which is a continuation in part of U.S. Ser. No. 142,692, filed Jan. 11, 1988, now abandoned; all of the above are hereby incorporated by reference herein.

BACKGROUND

In nature, the organic constituents of animals, microorganisms and plants are made up of chiral molecules, or molecules which exhibit handedness. Enantiomers are stereoisomers or chiral molecules whose configurations (arrangements of constituent atoms) are non-superimposed mirror images of each other; absolute configurations at chiral centers are determined by a set of rules by which a priority is assigned to each substituent and are designated R and S. The physical properties of enantiomers are identical, except for the direction in which they rotate the plane of polarized light: one enantiomer rotates plane-polarized light to the right and the other enantiomer rotates it to the left. However, the magnitude of the rotation caused by each is the same.

The chemical properties of enantiomers are also identical, with the exception of their interactions with optically active reagents. Optically active reagents interact with enantiomers at different rates, resulting in reaction rates which may vary greatly and, in some cases, at such different rates that reaction with one enantiomer or isomer does not occur. This is particularly evident in biological systems, in which stereochemical specificity is the rule because enzymes (biological catalysts) and most of the substrates on which they act are optically active.

A mixture which includes equal quantities of both enantiomers is a racemate (or racemic modification). A racemate is optically inactive, as a result of the fact that the rotation of polarized light caused by a molecule of one isomer is equal to and in the opposite direction from the rotation caused by a molecule of its enantiomer. Racemates, not optically active compounds, are the products of most synthetic procedures. Because of the identity of most physical characteristics of enantiomers, they cannot be separated by such commonly used methods as fractional distillation (because they have identical boiling points), fractional crystallization (because they are equally soluble in a solvent, unless it is optically active) and chromatography (because they are held equally tightly on a given adsorbent, unless it is optically active). As a result, resolution of a racemic mixture into enantiomers is not easily accomplished and can be costly and time consuming.

Recently, there has been growing interest in the synthesis of chiral compounds because of the growing demand for complex organic molecules of high optical purity, such as insect hormones and pheromones, prostaglandins, antitumor compounds, and other drugs. This is a particularly critical consideration, for example, for drugs, because in living systems, it often happens that one enantiomer functions effectively and the other enantiomer has no biological activity and/or interferes with the biological function of the first enantiomer.

In nature, the enzyme catalyst involved in a given chemical reaction ensures that the reaction proceeds asymmetrically, producing only the correct enantiomer (i.e., the enantiomer which is biologically or physiologically functional). This is not the case in laboratory synthesis, however, and, despite the interest in and energy expended in developing methods by which asymmetric production of a desired chiral molecule (e g., of a selected enantiomer) can be carried out, there has been only limited success.

In addition to resolving the desired molecule from a racemate of the two enantiomers, it is possible, for example, to produce selected asymmetric molecules by the chiral pool or template method, in which the selected asymmetric molecule is "built" from pre-existing, naturally-occurring asymmetric molecules. Asymmetric homogeneous hydrogenation and asymmetric epoxidation have also been used to produce chiral molecules. Asymmetric hydrogenation is seen as the first manmade reaction to mimic naturally-occurring asymmetric reactions. Sharpless, K. B., *Chemisry in Britain*, January 1986, pp 38–44; Mosher. H. S. and J. D. Morrison, *Science*, 221:1013–1019 (1983); Maugh, T. H., *Science*, 221:351–354 (1983); Stinson, S., *Chemistry and Engineering News*, :24 (Jun. 2, 1986).

Presently-available methods of asymmetric synthesis are limited in their applicability, however. Efficient catalytic asymmetric synthesis reactions are very rare; and they usually require a directing group and thus are substrate limited. Because such reactions are rare and chirality can be exceptionally important in drugs, pheromones and other biologically functional compositions, a catalytic method of asymmetric dihydroxylation would be very valuable. In addition, many naturally-occurring products are dihydroxylated or can be easily derived from a corresponding vicinal diol derivative.

SUMMARY OF THE INVENTION

Olefins or alkenes with or without proximal heteroatom-containing functional groups, are asymmetrically dihydroxylated, oxyaminated or diaminated using an osmium-catalyzed process which is the subject of the present invention. Chiral ligands which are novel alkaloid derivatives, particularly quinidine derivatives, dihydroquinidine derivatives, quinine derivatives, dihydroquinine derivatives or salts thereof, useful in the method of the present invention are also the subject of the present invention.

One embodiment of the invention pertains to compositions that can be used as chiral ligands in the asymmetric dihydroxylation of olefins. These compositions have three moieties covalently linked together in a prescribed configuration. One moiety is an alkaloid or alkaloid derivative. A second moiety is an organic substituent whose molecular weight is at least 300 daltons. In a preferred embodiment, the organic substituent is an alkaloid or alkaloid derivative, often identical to the substance that constitutes the first moiety. The first and second moieties are connected to each other through an intervening planar aromatic spacer group. This spacer group is covalently bonded to both the alkaloid or alkaloid derivative and the organic substituent. Additionally, the spacer group separates the first and second moieties from each other.

Another embodiment of the invention pertains to asymmetric dihydroxylation of olefins by reactions that utilize the chiral ligands described in the previous paragraph. In these reactions, an olefin, an organic solvent, an aqueous solution, a base, an osmium-containing catalyst, a ferricyanide salt and a chiral ligand are combined under conditions appropriate for asymmetric addition to occur. The chiral ligand (termed a chiral auxiliary) is an alkaloid or alkaloid derivative and an organic substituent of at least 300 daltons molecular weight linked together through a planar aromatic spacer group. In a preferred embodiment, the chiral auxiliary, organic solvent, aqueous solution, base, osmium-containing catalyst and ferricyanide salt are combined, the olefin is added and the resulting combination is maintained under conditions appropriate for asymmetric dihydroxylation of the olefin to occur.

DETAILED DESCRIPTION OF THE INVENTION

Asymmetric epoxidation has been the subject of much research for more than ten years. Earlier work demonstrated that the titanium-tartrate epoxidation catalyst is actually a complex mixture of epoxidation catalysts in dynamic equilibrium with each other and that the main species present (i.e., the 2:2 structure) is the best catalyst (i.e., about six times more active than titanium isopropoxide hearing no tartrate). This work also showed that this rate advantage is essential to the method's success because it ensures that the catalysis is channeled through a chiral ligand-bearing species.

The reaction of osmium tetroxide ($OsO_4$) with olefins is a highly selective and reliable organic transformation. It has long been known that this reaction is accelerated by nucleophilic ligands. Criegee, R. *Justus Liebigs Ann. Chem.*, 522:75 (1936); Criegee, R. et al., *Justus Liebigs Ann. Chem.*, 550:99 (1942); VanRheenen et al., *Tetrahedron Lett.*, 1973 (1976). It has now been shown that a highly effective osmium-catalyzed process can be used to replace previously known methods, such as the stoichiometric asymmetric osmylation method. Hentges, S. G. and K. B. Sharpless, *Journal of the American Chemical Society*, 102:4263 (1980). The method of the present invention results in asymmetric induction and enhancement of reaction rate by binding of a selected ligand. Through the use of the ligand-accelerated catalytic method of the present invention, asymmetric dihydroxylation, asymmetric diamination or asymmetric oxyamination can be effected.

As a result of this method, two hydroxyl groups are stereospecifically introduced into (imbedded in) a hydrocarbon framework, resulting in cis vicinal dihydroxylation. The new catalytic method of the present invention achieves substantially improved rates and turnover numbers (when compared with previously-available methods), as well as useful levels of asymmetric induction. In addition, because of the improved reaction rates and turnover numbers, less osmium catalyst is needed in the method of the present invention than in previously-known methods. As a result, the expense and the possible toxicity problem associated with previously-known methods are reduced. Furthermore, the invention allows the recovery and reuse of osmium, which reduces the cost of the process.

The method of the present invention is exemplified below with particular reference to its use in the asymmetric dihydroxylation of E-stilbene ($C_6H_5CH:CHC_6H_5$) and trans-3-hexene ($CH_3CH_2CH:CHCH_2CH_3$). The method can be generally described as presented below and that description and subsequent exemplification not only demonstrate the dramatic and unexpected results of ligand-accelerated catalysis, but also make evident the simplicity and effectiveness of the method.

Figure 1:
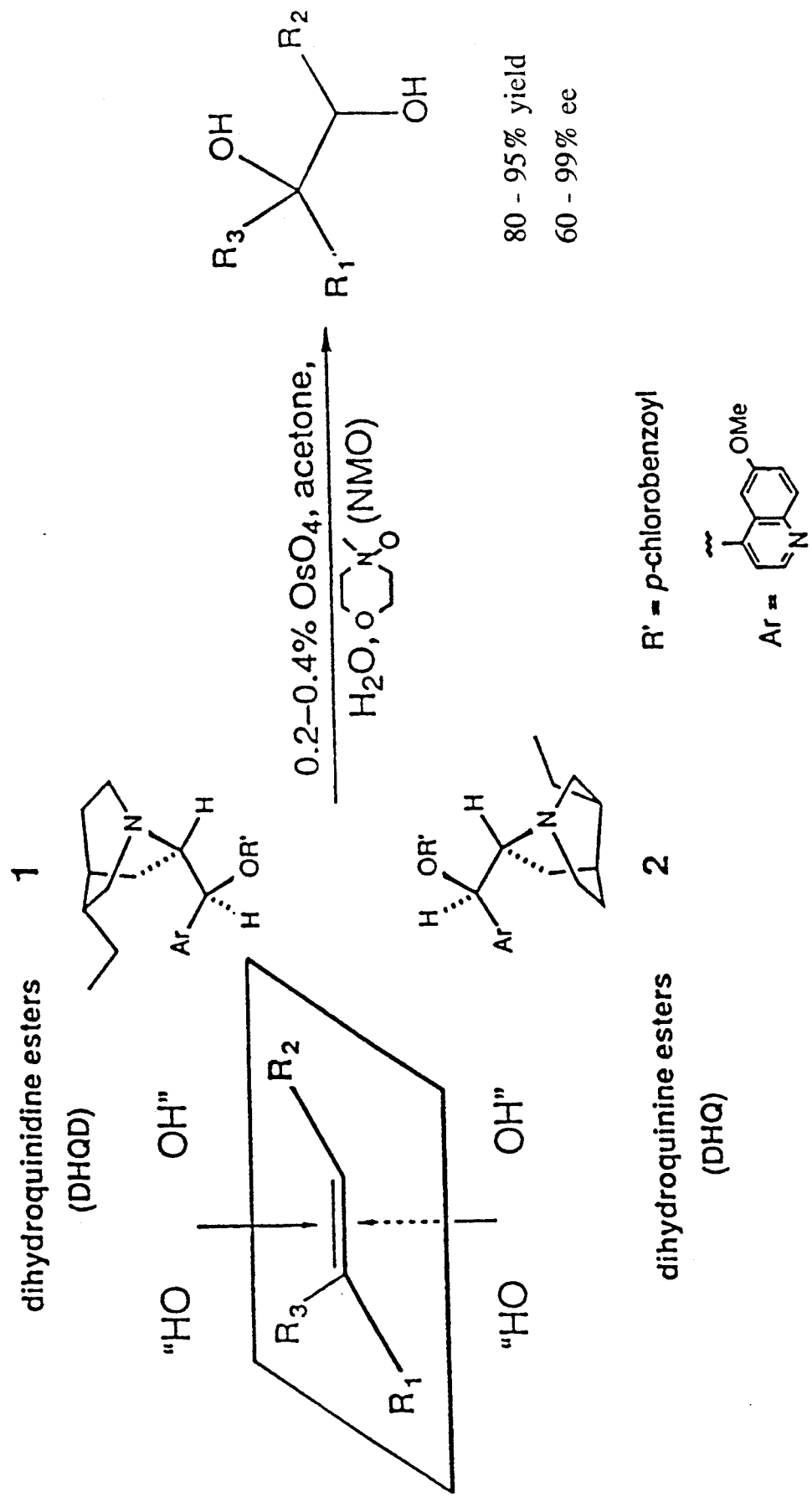
FIG. 1 is a schematic representation of asymmetric dihydroxylation via ligand-accelerated catalysis which is carried out by the method of the present invention.

The asymmetric dihydroxylation method of the present invention is represented by the scheme illustrated in FIG. 1. According to the method of the present invention, asymmetric dihydroxylation of a selected olefin is effected as a result of ligand-accelerated catalysis. That is, according to the method, a selected olefin is combined, under appropriate conditions, with a selected chiral ligand (which in general will be a chiral substituted quinuclidine), an organic solvent, water, an oxidant and osmium tetroxide and, optionally, a compound which promotes hydrolysis of the products from the osmium. Acids or bases can be used for this purpose. In one embodiment, a selected olefin, a chiral ligand, an organic solvent, water and an oxidant are combined; after the olefin and other components are combined, $OsO_4$ is added. The resulting combination is maintained under conditions (e.g., temperature, agitation, etc.) conducive for dihydroxylation of the olefin to occur. Alternatively, the olefin, organic solvent, chiral ligand, water and $OsO_4$ are combined and the oxidant added to the resulting combination. These additions can occur very close in time (i.e., sequentially or simultaneously).

In one embodiment of the present invention, components of the reaction mixture are combined, to form an initial reaction combination, and olefin is added slowly to it, generally with frequent or constant agitation, such as stirring. In this embodiment, designated the "slow addition" method, organic solvent, chiral ligand, water, OsO₄ and the oxidant are combined. The olefin can then be slowly added to the other reactants. It is important that agitation, preferably stirring, be applied during the olefin addition. Surprisingly, for many, if not most olefins, slow addition of the olefin to the initial combination results in much better enantiomeric excess (ee), and a faster race of reaction than the above-described method (i.e., that in which all the olefin is present at the beginning of the reaction). The beneficial effects (i.e., higher ee's) of slow olefin addition are shown in Table 5 (Column 6). A particular advantage of this slow-addition method is that the scope of the types of olefins to which the asymmetric dihydroxylation method can be applied is greatly broadened. That is, it can be applied to simple hydrocarbon olefins bearing no aromatic substituents, or other functional groups. In this process, the olefin is added slowly (e.g., over time), as necessary to maximize ee. This method is particularly valuable because it results in higher ee's and faster reaction times.

In another embodiment of the present method, the chiral ligands are immobilized or incorporated into a polymer, thereby immobilizing the ligands. Both monomers and polymers of alkaloid ligands can be immobilized. The immobilized ligands form a complex with the osmium catalyst, which results in formation of an osmium catalyst complex which can be recovered after the reaction. The OsO₄-polymer complex is recoverable and can be used for iterative processes without washing or other treatment. The complex can be recovered, for example, by filtration or centrifugation. By employing alkaloid derivatives, heterogeneous catalytic asymmetric dihydroxylation is achieved with good to excellent enantioselectivities in the dihydroxylation of olefins.

Alternatively, alkaloid polymers can be used as ligands. Alkaloid polymers which can be used are described, for example, by Kobayashi and Iwai in *Tetrahedron Letters*, 21:2167-2170 (1980) and *Polymer Journal*, 13(3) 263-271 (1981); by vonHermann and Wynberg in *Helvetica Chimica Acta*, 60:2208-2212 (1977); and by Hodge et al., *J. Chem. Soc. Perkin Trans. I*, (1983) pp. 2205-2209. Both alkaloid polymer liganus and immobilized ligands form a complex with the osmium in situ. The term "polymeric", as used herein is meant to include monomers or polymers of alkaloid ligands which are chemically bonded or attached to a polymer carrier, such that the ligand remains attached under the conditions of the reaction, or ligands which are copolymerized with one or more monomers (e.g., acrylonitrile) to form a co-polymer in which the alkaloid is incorporated into the polymer, or alkaloid polymers as described above, which are not immobilized or copolymerized with another polymer or other carrier.

Industrial scale syntheses of optically active vicinal diols are possible using polymeric ligands. The convenience and economy of the process is enhanced by recycling the alkaloid-OsO₄ complex. This embodiment of the present method allows efficient heterogeneous asymmetric dihydroxylation utilizing polymeric or immobilized cinchona alkaloid derivatives.

Polymeric cinchona alkaloids which are useful in the present method can be prepared by art-recognized techniques. See, for example, Grubhofer and Schleith, *Naturwissenschaften*, 40:508 (1953); Yamauchi et al., *Bull. Chem. Soc. Jpn.*, 44:3186 (1971); Yamauchi et al., *J. Macromal. Sci. Chem.*, A10:981 (1976). A number of different types of polymers that incorporate dihydroquinidine or dihydroquinine derivatives can be used in this process. These polymers include: (a) co-polymers of cinchona alkaloid derivatives with co-polymerizing reagents, such as vinyl chloride, styrene, acrylamide, acrylonitrile, or acrylic or methacrylic acid esters; (b) cross-linked polymers of cinchona alkaloid derivatives with cross-linking reagents, such as 1,4-divinylbenzene, ethylene glycol bismethacrylate; and (c) cinchona alkaloid derivatives covalently linked to polysiloxanes. The connecting point of the polymer backbone to the alkaloid derivative can be at C(10), C(11), C(9)-O,N(1'), or C(6')-O as shown below for both quinidine and quinine derivatives. Table 3 shows the examples of the monomeric alkaloid derivatives which can be incorporated in the polymer system.

For example, a polymer binding dihydroquinidine was prepared by copolymerizing 9-(10-undecenoyl)-dihydroquinidine in the presence of acrylonitrile (5 eq); a 13% yield was obtained exhibiting 4% alkaloid incorporation. This polymer, an acrylonitrile co-polymer of 9-(10-undecenoyl)-10,11-dihydroquinidine, is shown as polymer 4 in Table 1, below. Three other polymers, an acrylonitrile co-polymer of 9-(4-chlorobenzoyloxy)quinine, (polymer 1, Table 3) an acrylonitrile co-polymer of 11-[2-acryloyloxy)ethylsulfinyl]-9-(4-chlorobenzoyloxy)--10,11-dihydroquinine (polymer 2, Table 1) and an acrylonitrile co-polymer of 11-[2-acryloyloxy)-ethylsulfonyl]-9-(N,N-dimethylcarbamoyl)-10,11-dihydroquinidine, (polymer 3, Table 1) were prepared according to the procedures of Inaguki et al., or slightly modified versions of this procedure. See, Inaguki et al., *Bull. Chem. Soc. Jpn.*, 60:4121 (1987). Using these polymers, the asymmetric dihydroxylation of trans-stilbene was carried out. The results are summarized in Table 1. Good to excellent asymmetric induction and reasonable reaction rates were observed. As shown in Table 1, reaction with polymer 2 exhibited the highest degree of asymmetric induction. The activity of the OsO₄-polymer complex is preserved after the reaction, thus allowing repetitive use of the complex. This reaction can be carried out with terminal and aliphatically substituted olefins to show good yields and enantioselectivities (for example, styrene with polymer 2, 60% ee, 68% yield and ethyltrans-2-octenoate with polymer 3, 60% ee, 85% yield) and the same process can be applied to a variety of different olefins.

TABLE 1

Heterogeneous Catalytic Asymmetric
Dihydroxylation of trans-Stilbene Using Variuos Polymeric
Alkaloids

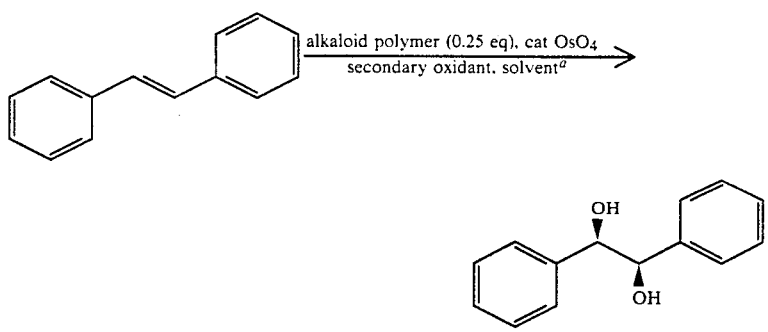

| Entry | Polymers | $OsO_4$ | Secondary Oxidant | Reaction Temp | Reaction Time | Yield (%) | ee (%) |
|---|---|---|---|---|---|---|---|
| 1 | 1 | 1 mol % | NMO | rt | 7d | 68 | — |
| 2 | 2 | 1 mol % | NMO | 10° C. | 2–3d | 81–87 | 85–93[b] |
| 3 | 2 | 1 mol % | NMO | rt | 24 h | 81 | 82 |
| 4 | 2 | —[c] | NMO | rt | 36 h | 75 | 78 |
| 5 | 3 | 1 mol % | NMO | 0° C. | 48 h | 85 | 80 |
| 6 | 3 | 1.25 mol % | $K_3Fe(CN)_6$ | rt | 18 h | 96 | 87 |
| 7 | 4 | 1 mol % | NMO | 10° C. | 48 h | 87 | 82 |
| 8 | 4 | 1.25 mol % | $K_3Fe(CN)_6$ | rt | 48 h | 91 | 86 |

[a]General procedure is set out in detail in Example 14. With N-methylmorpholine-N-oxide (NMO) acetone/water (10/1, v/v) was the solvent and ferricyanide tert-butyl alcohol/water (1/1, v/v) was used as solvent.
[b]Results vary slightly depending on different batches of polymer 2.
[c]Reaction was carried out with polymer 2 which had been used in entry 3 without further addition of $OsO_4$.

In another embodiment of the present method, an additive which accelerates hydrolysis of the osmate ester intermediates can, optionally, be added to the reaction combination. These additives can be acids or bases, for example. Bases are preferred for this purpose. For example, soluble, carboxylic acid salts with organic-solubilizing counter-ions (e.g., tetraalkyl ammonium ions) are useful. Carboxylate salts which are preferred in the present reaction are soluble in organic media and in organic/aqueous co-solvent systems. For example, tetraethyl ammonium acetate has been shown to enhance the reaction rate and ee of some olefins (Table 5). The additive does not replace the alkaloid in the reaction. Compounds which can be used include benzyltrimethylammoniumacetate, tetramethylammonium acetate and tetraethylammonium acetate. However, other oxyanion compounds (e.g., sulfonates, carbonates, borates or phosphates) may also be useful in hydrolyzing the osmate ester intermediates. The compound can be added to the reaction combination of organic solvent, chiral ligand, water and $OsO_4$ in a reaction vessel before olefin addition. It is important to agitate (e.g., by stirring) the reaction combination during olefin addition. The additive can also be added to the reaction combination, described above, wherein all of the olefin is added at the beginning of the reaction. In one embodiment, the amount of additive is generally approximately 2 equivalents; in general from about 1 to about 4 equivalents will be used.

In another embodiment of the present invention, the process can be run in an organic non-polar solvent such as toluene. This embodiment is particularly useful in the slow addition method. Preferably, a carboxylate compound which accelerates hydrolysis of the osmate ester intermediates (e.g., tetraethyl- or tetramethyl ammonium acetate) is added. This embodiment is designated the "phase transfer" method. In this embodiment olefins which are not soluble, or have limited solubility, in mixtures of acetone/water or acetonitrile/water, are dissolved in toluene and then added slowly a mixture of organic solvent, chiral ligand, water and $OsO_4$. The carboxylate salt serves the dual function of solubilizing the acetate ion in the organic phase where it can promote hydrolysis of the osmate ester, and carrying water associated with it into the organic phase, which is essential for hydrolysis. Higher ee's are obtained with many substrates using this method.

In a further embodiment of the present invention, a boric acid or a boric acid derivative (R-B(OH)$_2$, R=alkyl, aryl or OH), such as boric acid itself (i.e., B(OH)$_3$) or phenylboric acid (i.e., Ph-B(OH)$_2$), can be added to the reaction mixture. In the slow addition method, the boric acid is added to the ligand—organic solvent—$OsO_4$ mixture prior to the addition of the olefin. The amount of boric acid added is an amount sufficient to form the borate ester of the diol produced in the reaction. Without wishing to be bound by theory, it is believed that the boric acid hydrolyzes the osmium ester and captures the diols which are generated in the reaction. Neither water nor a soluble carboxylate such as tetraalkyl ammonium carboxylate, is required to hydrolyze the osmium ester in the present reactions. Because the presence of water can make the isolation and recovery of water-soluble diols difficult, the addition of a boric acid makes isolation of these diols easier. Especially, in the case of an aryl or alkyl boric acid, it is easy because, in place of the diol, the product is the cyclic borate ester which can be subsequently hydrolyzed to the diol. Iwasawa et al., *Chemistry Letters*, pp. 1721–1724 (1988). The addition of a boric acid is particularly useful in the slow addition method.

In another embodiment of the present method, oxidants such as potassium hexacyanoferrate (III) (potassium ferricyanide, $K_3Fe(CN)_6$) is added to the reaction as a reoxidant. In a preferred embodiment, at least two equivalents of the oxidant (based on the amount of olefin substrate) is added to the reaction. It is also preferable that an equivalent amount of a base, such as potassium carbonate ($K_2CO_3$), is added in conjunction with the reoxidant. High enantioselectivities are obtained in catalytic asymmetric dihydroxylations using $K_3Fe(CN)_6$ as the reoxidant.

The use of potassium ferricyanide in a stoichiometric amount as an oxidant for non-asymmetric osmium-catalyzed dihydroxylation of olefins was reported by Minato, Yamamoto and Tsuji, in *J. Org. Chem.*, 55:766 (1990). The addition of $K_3Fe(CN)_6$ (in conjunction with the base) results in an improvement in the ability of the Tsuji's catalytic system to turn over, even in the presence of quinuclidine, a ligand which strongly inhibits catalysis when other oxidants are used, e.g. N-methylmorpholine-N-oxide (NMO). In the present embodiment, potassium ferricyanide and potassium carbonate were added to the present cinchona alkaloid-based asymmetric dihydroxylation process and the outcome was unexpected (i.e. not just another way to reoxidize the osmium and/or achieve better turnover with difficult substrates). As shown in Table 2, the use of potassium ferricyanide/potassium carbonate in place of NMO leads to across-the-board increases in the level of asymmetric induction for most olefins. The first two columns of data shown in Table 2 are for results employing NMO with and without "slow addition" of olefin, respectively. The third column reveals the results obtained using $K_3Fe(CN)_6$ with the same substrates and without "slow addition" of the olefin. The improvements of enantioselectivity are great as evidenced by the fact that the previous results (shown in Table 2) were obtained at 0° C. while the ferricyanide experiments were performed at room temperature. The ferricyanide reactions can be run at a range of temperatures, however, depending upon the substrate.

TABLE 2

Percentage enatiomeric excesses of diols obtained in the asymmetric dihydroxylation of olefins under different catalytic conditions using dihydroquinidine p-chlorobenzoate as the chiral ligand.

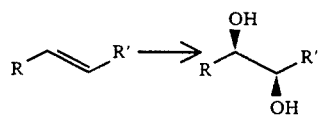

| entry | olefins | NMO[a] | | $K_3Fe(CN)_6$[b] |
|---|---|---|---|---|
| | | ee (%) (slow addition) | ee (%) (no slow addition) | ee (%) (no slow addition) |
| 1 | styrene | 60 | 56 | 73 |
| 2 | stilbene | 95 | 78 | 99 |
| 3 | β-methylstyrene | 86 | 65 | 91 |
| 4 | cinnamyl acetate | 79 | 76 | 91 |
| 5 | methyl cinnamate | 86 | 60 | 95 |
| 6 | alkene | 69 | 20 | 74 |

[a]Reactions were carried out in acetone-water. 10:1 v/v. at 0° C.
[b]Reactions were carried out in tert-butyl alcohol-water 1:1 v/v, at ambient temperature.
In all cases the isolated yield was 85% -95%.

The amount of water added to the reaction mixture is an important factor in the present method. The optimum amount of water to be added can be determined empirically and, in general, should be that amount which results in maximum ee. Generally, approximately 10 to 16 equivalents of water can be added, preferably 13 to 14 equivalents should be used.

An olefin of interest can undergo asymmetric dihydroxylation according to the present invention. For example, any hydrocarbon containing at least one carbon-carbon double bond as a functional group can be asymmetrically dihydroxylated according to the subject method. The method is applicable to any olefin of interest and is particularly well suited to effecting asymmetric dihydroxylation of prochiral olefins (i.e., olefins which can be converted to products exhibiting chirality or handedness). In the case in which the method of the present invention is used to asymmetrically dihydroxylate a chiral olefin, one enantiomer will be more reactive than the other. As a result, it is possible to separate or kinetically resolve the enantiomorphs. That is, through use of appropriately-selected reactants, it is possible to separate the asymmetrically dihydroxylated product from the unreacted starting material and both the product and the recovered starting material will be enantiomerically enriched.

The chiral ligand used in the asymmetric dihydroxylation method will generally be an alkaloid, or a basic nitrogenous organic compound, which is generally heterocyclic. The chiral ligand can be a naturally occurring compound, a purely synthetic compound or a salt thereof, such as a hydrochloride salt. The optimum derivative which is used can be determined based upon the process conditions for each reaction. Examples of alkaloids which can be used as the chiral ligand in the asymmetric dihydroxylation method include cinchona alkaloids, such as quinine, quinidine, cinchonine, and cinchonidine. Examples of alkaloid derivatives useful in the method of the present invention are shown in Table 3. As described in detail below, the two cinchona alkaloids quinine and quinidine act more like enantiomers than like diastereomers in the scheme represented in FIG. 1.

As represented in FIG. 1, and as shown by the results in Table 4, dihydroquinidine derivatives (represented as DHQD) and dihydroquinine derivatives (represented as DHQ) have a pseudo-enantiomeric relationship in the present method (DHQD and DHQ are actually diastereomers). That is, they exhibit opposite enantiofacial selection. Such derivatives can be, for example, esters or ethers, although other forms can be used. The choice of derivative depends upon the process. When dihydroquinidine is used as the ligand, delivery of the two hydroxyl groups takes place from the top or upper face (as represented in FIG. 1) of the olefin which is being dihydroxylated. That is, in this case direct attack of the re- or re,re- face occurs. In contrast, when the dihydroquinine derivative is the ligand used, the two hydroxyl groups are delivered from the bottom or lower (si- or si,si-face) face of the olefin, again as represented in FIG. 1. This is best illustrated by reference to entries 1, 2 and 5 of Table 4. As shown, when DHQD (dihydroquinidine esters) is used, the resulting diol has an R or R,R configuration and when ligand 2 (dihydroquinine esters) is used, the resulting diol has an S or S,S configuration.

TABLE 3

Alkaloid Derivatives

| R | Dihydroquinidine Derivative | Yield (%) | % ee |
|---|---|---|---|
| 3-ClC$_6$H$_4$ | 3-chlorobenzoyl | 89 | 96.5 |
| 2-MeOC$_6$H$_4$ | 2-methoxybenzoyl | 89 | 96 |
| 3-MeOC$_6$H$_4$ | 3-methoxybenzoyl | 87 | 96.7 |
| 2-C$_{10}$H$_7$ | 2-napthoyl | 95.4 | 98.6 |
| C$_6$H$_{11}$ | cyclohexanoyl | 90 | 91 |
| 4-PhC$_6$H$_4$ | 4-phenylbenzoyl | 89 | 96 |
| 2,6-(MeO)$_2$C$_6$H$_3$ | 2,5-dimethoxybenzoyl | 88 | 92 |
| 4-MeOC$_6$H$_4$ | 4-methoxyenzoyl | 91 | 97.6 |
| 4-ClC$_6$H$_4$ | 4-chlorobenzoyl | 93 | 99 |
| 2-ClC$_6$H$_4$ | 2-chlorobenzoyl | 87 | 94.4 |
| 4-NO$_2$C$_6$H$_4$ | 4-nitrobenzoyl | 71 | 93 |
| C$_6$H$_5$ | benzoyl | 92 | 98 |
| Me$_2$N | dimethylcarbamoyl | 96 | 95 |
| Me | acetyl | 72 | 94 |
| MeOCH$_2$ | α-methoxyacetyl | 66 | 93 |
| AcOCH$_2$ | α-acetoxyacetyl | 96 | 82.5 |
| Me$_3$C | trimethylacetyl | 89 | 86.5 |

The example below is a phosphoryl derivative and therefore differs from the carboxylic acid ester derivatives shown above: the phosphorus atom is directly bound to the oxygen atom of the alkaloid.

| Ph$_2$P(O) | diphenylphosphinic ester | 69 | 97.5 |

TABLE 4

| Olefins | ligand: ee$^a$; confgn. of diol |
|---|---|
|  | DHQD; 20%, (70%, 10 h); RR<br>DHQ; (60%, 16 h); SS |
| n-Bu, n-Bu | DHQD; (70%, 120 h) |
| n-C$_5$H$_{11}$ | DHQD; (69%, 30 h); RR<br>DHQ; (63%, 30 h); SS |
|  | DHQD; 12%, (46%, 24 h).<br>(76%, 24 h + 1 eq OAc) |
|  | DHQD; 37.5% |

TABLE 4-continued

| Olefins | ligand; ee[a]; confgn. of diol |
|---|---|
| (CH₃)₂C=CH-CH₂-CH₂-CH₃ | DHQD; (46%, 24 h, rt) |
| CH₃-CH=C(CH₃)-CH₂-CH₂-CH₃ | DHQD; (40%, 24 h, rt) |
| cyclohexyl-CH=CH₂ | DHQD; 46%, (50%, 20 h); R |
| cyclooctyl-CH=CH₂ | DHQD; 50% |
| (CH₃)₃C-CH=CH₂ | DHQD; 40% |
| Cl-CH₂-CH=CH-CH₂-Cl | DHQD; 35%, (40%, 12 h) |
| styrene | DHQD; 56%, (61%, 5 h); R<br>DHQ; 54%; S |
| 2-methylstyrene | DHQD; 53% |
| 2,6-dimethylstyrene | DHQD; 65% |
| 2,5-dimethylstyrene | DHQD; 63% |
| trans-β-methylstyrene | DHQD; 65%, (86%, 5 h); RR<br>DHQ; 55%, (80%, 5 h); SS |
| cis-β-methylstyrene | DHQD; 0-10% |
| α-methylstyrene | DHQD; 33%; R |
| β,β-dimethylstyrene | DHQD; 34%, (53%, 24 h) |

TABLE 4-continued

| Olefins | ligand; ee<sup>a</sup>; confgn. of diol |
|---|---|
| 4-nitrostyrene (O₂N-C₆H₄-CH=CH₂) | DHQD; 51% |
| 4-methoxystyrene (MeO-C₆H₄-CH=CH₂) | DHQD; 67% |
| 2-vinylfuran | DHQD; 40% |
| stilbene (Ph-CH=CH-Ph) | DHQD; 80%; 92% in the presence of 2 eq. OAc; RR<br>DHQ; 79%; SS |
| 1-phenylcyclohexene | DHQD; 10%, (78%, 26 h), (81%, 16 h + 1 eq OAc)<br>DHQ; (73%, 26 h) |
| cinnamyl acetate (Ph-CH=CH-CH₂-OAc) | DHQD; 76%; RR |
| cinnamyl benzoate (Ph-CH=CH-CH₂-OCOPh) | DHQD; 80% |
| cinnamyl chloride (Ph-CH=CH-CH₂-Cl) | DHQD; 60%, (78%, 10 h) |
| allylbenzene (Ph-CH₂-CH=CH₂) | DHQD; 20% |
| (E)-1-phenyl-2-butene (Ph-CH₂-CH=CH-CH₃) | DHQD; (44%, 10 h) |
| allyl phenyl ether (PhO-CH₂-CH=CH₂) | DHQD; 34% |
| 2-methylallyl phenyl ether | DHQD; 27% |
| methyl (E)-2-octadecenoate (nC₁₅H₃₁-CH=CH-CO₂Me) | DHQD; 38% |

TABLE 4-continued
| Olefins | ligand; ee[a]; confgn. of diol |
|---|---|
| 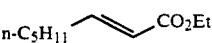 n-C₅H₁₁—CH=CH—CO₂Et | DHQD; 47.4%, (67%, 31 h) |
| 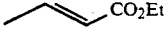 CH₃—CH=CH—CO₂Et | DHQD; 53% |
| 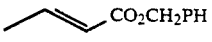 CH₃—CH=CH—CO₂CH₂PH | DHQD; 45% |
| 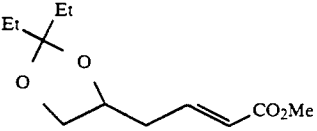 | DHQD; (52% de, 31 h) |
| 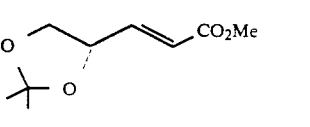 | DHQD; (70% de, 42 h) |
| 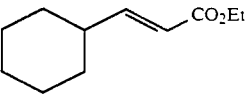 | DHQD; 74.3% |
| 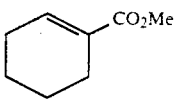 | DHQD; (36%, 24 h + OAc, rt) |
| 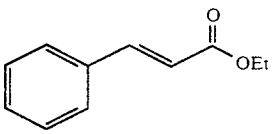 | DHQD; 92% |
| 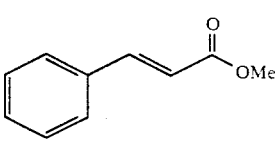 | DHQD; 91% |
| 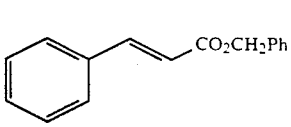 | DHQD; 80-85% |
| 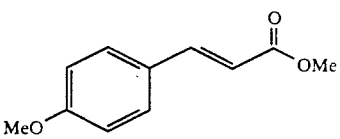 | DHQD; <60%, (80%, slow addition) |
| 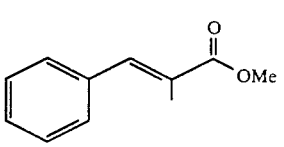 | DHQD; (38%, toluene-water, 24 h + OAc, rt) |
| 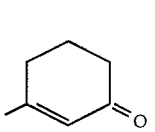 | DHQD; (10%, 24 h, rt) |

TABLE 4-continued

| Olefins | ligand: ee[a]; confgn. of diol |
|---|---|
| 1-acetylcyclohexene | DHQD; (36%, 24 h + OAc, rt) |
| methyl-cyclohexenyl ethyl acetal | DHQD; (37%, 12 h + OAc) |
| CH₂=CH-CH(OEt)₂ | DHQD; 27%, (31%, 13 h) |
| n-C₇H₁₅-CH=CH-CH₂-O-CH(O)-Et | DHQD: (56%, 20 h) (66%, 20 h + OAc) |
| n-C₅H₁₁-CH=CH-C(Me)(O-)(O-)Et | DHQD; (46%, 18 h) (50%, 18 h + OAc) |
| Ph-CH=CH-CH(OMe)₂ | DHQD: 75%, 18 h) (83%, 18 h + OAc) |
| Ph-CH=CH-C(Me)(O-)(O-)Et | DHQD: (60%, 10 h) (89%, 10 h + OAc) |
| Ph-CH=CH-C(Ph)(O-)(O-)Et | DHQD; (85%, 20 h) (87%, 20 h + OAc) |
| Et-CH=C(OSiMe₃)-Pr | DHQD; (27%, 23 h + OAc) |
| Ph-C(OSiMe₃)=CH-Me | DHQD; (72%, 23 h) (78%, 23 h + OAc) |

[a]Enantiomeric excesses in parentheses were obtained with slow addition of olefin over a period of time indicated and with stirring at 0°C. except otherwise stated. Tetraethylammonium acetate tetrahydrate were added in some cases as indicated.

TABLE 5

Enantiomeric excesses obtained in the asymmetric dihydroxylation of olefins under different conditions

| entry | olefin | stoichiometric[a] | catalytic[b] (original) | catalytic[c] (acetate) | catalytic[d] (slow addition) |
|---|---|---|---|---|---|
| 1 | styrene | 61 | 56 | 61 | 60 (5 h) |
| 2 | β-methylstyrene | 87 | 65 | 73 | 86 (5 h) |
| 3 | 1-phenylcyclohexene | 79 | 8[e] | 52 | 78 (26 h)[f] |
| 4 | 2,5-dimethyl-3-hexene | 80 | 12[g] | 61 | 46 (24 h)[h] |
| | | | | | 76 (24 h + OAc) |
| 5 | trans-3-hexene | 69 | 20 | 64 | 70 (10 h) |

[a]All stoichiometric reactions were carried out in acetone-water, 10:1 v/v, at 0° C. and at a concentration of 0.15M in each reagent.
[b]All reactions were carried out at 0° C. according to the original procedure reported in ref. 1(a).
[c]All reactions were carried out exactly as described in ref. 1(a) (i.e. without slow addition) except that 2 eq of Et₄NOAc—4H₂O were present.
[d]All reactions were carried out at 0° C. as described in note 2 for trans-3-hexene with an alkaloid concentration of 0.25M. The period for slow addition of the olefin is indicated in parentheses. The ee's shown in the Table were obtained with dihydroquinidine p-chlorobenzoate as the ligand. Under the same conditions, the pseudoenantiomer, dihydroquinine p-chlorobenzoate, provides products with ee's 5-10% lower. In all cases the isolated yield was 85-95%.
[e]This reaction took 7 days to complete.
[f]With an addition period of 16 h. ee's of 63 and 65% were obtained at 0° C. and 20° C., respectively; with the combination of slow addition over a period of 16 h and the presence of 1 eq of Et₄NOAc—4H₂O at 0° C., an ee of 81% was realized.
[g]This reaction took 5 days to complete.
[h]When the reaction was carried out at 20° C. and the olefin was added over a period of 24 h, an ee of 59% was obtained.

Because of this face selection rule or phenomenon, it is possible, through use of the present method and the appropriate chiral ligand, to pre-determine the absolute configuration of the dihydroxylation product.

As is also evident in Table 4, asymmetric dihydroxylation of a wide variety of olefins has been successfully carried out by means of the present invention. Each of the embodiments described results in asymmetric dihydroxylation, and the "slow addition" method is particularly useful for this purpose. In each of the cases represented in the Table in which absolute configuration was established, the face selection "rule" (as interpreted with reference to the orientation represented in FIG. 1) applied: use of DHQD resulted in attack or dihydroxylation occurring from the top or upper face and use of DHQ resulted in attack or dihydroxylation occurring from the bottom or lower face of the olefin. This resulted, respectively, in formation of products having an R or R,R configuration and products having an S or S,S configuration.

In a preferred embodiment of the present method, aromatic ethers of various cinchona alkaloids are used as ligands. The term "aromatic ethers" includes aryl ethers and heterocyclic ethers. A high level of asymmetric induction can be obtained using aromatic ethers of dihydroquinidine or dihydroquinine as ligands. For example, aromatic ethers having the following formula are particularly useful:

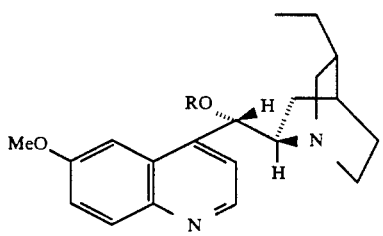

wherein R is phenyl, naphthyl, or o-methoxyphenyl. The stoichiometric asymmetric dihydroxylation of various dialkyl substituted olefins was performed using the phenyl ether derivative of dihydroquinidine. The results are shown in Table 6.

TABLE 6

Stoichiometric Asymmetric Dihydroxylation
Phenyl Ether Dihydroquinidine

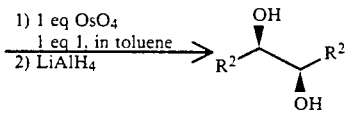

| Entry | Olefins | Reaction temp (°C.) | % ee[a] | % ee[a] with 3 (for comparison) |
|---|---|---|---|---|
| 1 |  | 0 | 85 | 71 |
| 2 |  | −78 | 95 |  |
| 3 |  | 0 | 88 | 73 |
| 4 |  | −78 | 93 |  |
| 5 |  | 0 | 89 | 79 |
| 6 |  | −78 | 94 |  |
| 7 | ~~~COOEt[b] | 0 | 90 | 67 |
| 8 | ~~~COOMe[b] | 0 | 97[c] | 77[c] |

[a] Enantiomeric excess was determined by GLC or HPLC analysis of the bis-Mosher ester derivatives.
[b] The reaction was worked up with NaHSO₃ in H₂O-THF.
[c] Diastereomeric excess.

The reaction was performed by adding 1 eq of olefin to a 1:1 mixture of OsO₄ and the ligand in dry toluene (0.1M) followed by a reductive work-up using lithium aluminum hydride (LiAlH₄) to yield the (R,R)-diol in 60–95% yield with good to excellent enantiomeric excess. Reactions with $\alpha,\beta$-unsaturated esters also proceeded with much improved enantio- and diastereoselectivities ($\geq 90\%$, as shown in entries 7 and 8, Table 6) using this ligand. By lowering the reaction temperature to −78° C., the reaction with straight chain dialkyl substituted olefins proceeded with very high enantioselectivities ($\geq 93\%$, as shown in entries 2, 4 and 6 of Table 6). In the several cases which were plotted the variance in ee with temperature closely followed the Arrhenius relationship.

Several dihydroquinidine aromatic ether derivatives were examined as chiral ligands for the asymmetric dihydroxylation of (E)-3-hexene, as shown in Table 7, below. Reactions with all of the aromatic ether derivatives tried exhibited higher enantioselectivities than the corresponding reaction with p-chlorobenzoate dihydroquinidine. The highest enantioselectivity was obtained with 9-O-(2'-methoxyphenyl)-dihydroquinidine (entry 2, Table 7).

TABLE 7

Stoichiometric Asymmetric Hydroxylation of (E)-3-hexene

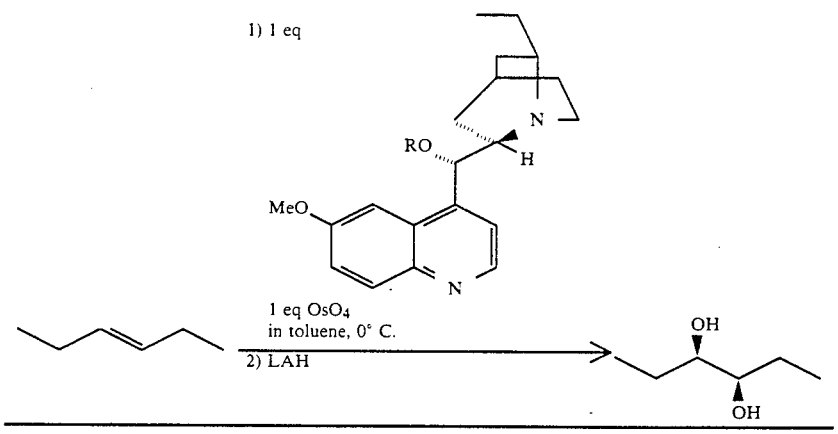

TABLE 7-continued

Stoichiometric Asymmetric Hydroxylation of (E)-3-hexene

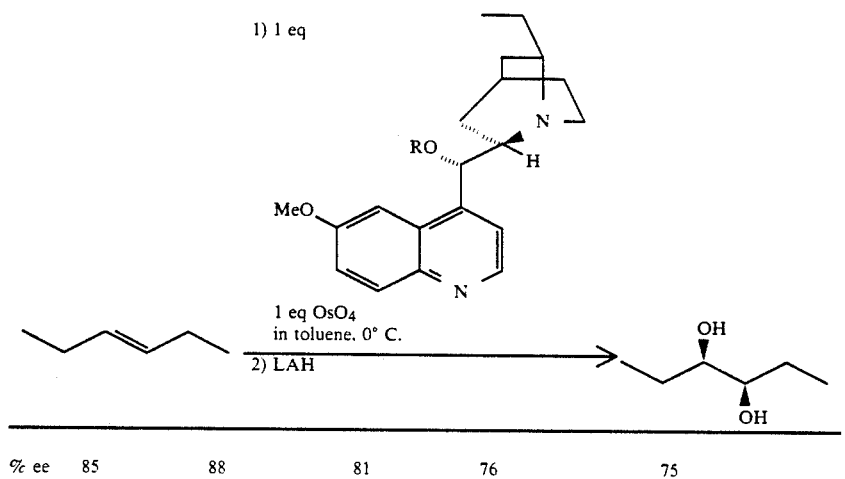

| % ee | 85 | 88 | 81 | 76 | 75 |

In one embodiment of the present method, aromatic ether ligands were used in the catalytic asymmetric dihydroxylation of (E)-3-hexene. In this embodiment, the results are summarized in Table 8. The catalytic asymmetric dihydroxylation reactions (entries 1–3, Table 8) were carried out by slow addition of (E)-3-hexene (1 eq) to a mixture of phenyl ether dihydroquinidine (0.25 eq), N-methylmorpholine N-oxide (NMO, 1.5 eq) and OsO$_4$ (0.004 eq) in acetone-water (10/1, v/v) at 0° C., followed by work-up with Na$_2$S$_2$O$_5$. The reaction proceeded faster upon addition of tetraethylammonium acetate (2 eq) to the reaction mixture (entry 4, Table 8). Potassium ferricyanide was added as the secondary oxidant (entries 5 and 6, Table 8). In these cases, slow addition of olefin was not required. To a mixture of (E)-3-hexane (1 eq), aromatic ether of dihydroquinidine (0.25 eq), K$_3$Fe(CN)$_6$ (3 eq) and potassium carbonate (K$_2$CO$_3$ 3 eq) in tert-butyl alcohol-water (1/1, v/v) was added OsO$_4$ (0.0125 eq); the resulting mixture was stirred at room temperature for 20 hours. Reductive work-up (with Na$_2$SO$_3$) gave the diol in 85-90% yield with essentially the same ee as that obtained in the stoichiometric reaction.

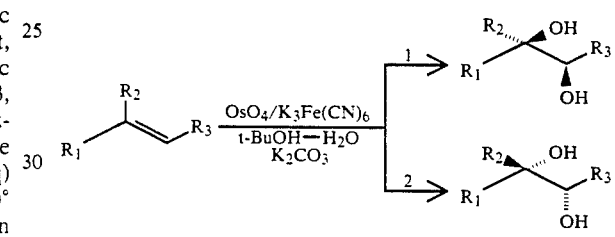

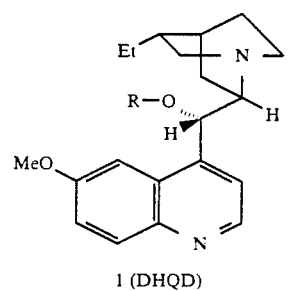

1 (DHQD)

2 (DHQ)

TABLE 8

Catalytic Asymmetric Dihydroxylation of (E)-3-hexene

| Entry | Ligand | OsO$_4$ | Secondary oxidant | Additive | Reaction Temp (°C.) | Reaction Time (hr) | % ee |
|---|---|---|---|---|---|---|---|
| 1 | 1 | 0.4 mol % | NMO | | 0 | 16 | 70 |
| 2 | 1 | 0.4 | NMO | | 0 | 30 | 75 |
| 3 | 1 | 0.4 | NMO | | 0 | 120 | 85 |
| 4 | 1 | 0.4 | NMO | Et$_4$NOAc | 0 | 16 | 82 |
| 5 | 1 | 1.25 | K$_3$Fe(CN)$_6$ | K$_2$CO$_3$ | rt | 20 | 83 |
| 6 | 2 | 1.25 | K$_3$Fe(CN)$_6$ | K$_2$CO$_3$ | rt | 20 | 89 |

Enantioselectivities in the dihydroxylation of dialkyl substituted olefins, which were previously only possible through the use of stoichiometric reagents at low temperature, can now be obtained in the catalytic asymmetric dihydroxylation using these aromatic ether ligands at room temperature. Disclosed here are two ligands which are particularly useful in the present method: the 9-O-(9′phenanthryl) ethers and the 9-O-(4′-methyl-2′-quinolyl) ethers of dihydroquinidine (1a and 1b below) and dihydroquinine (2a and 2b below).

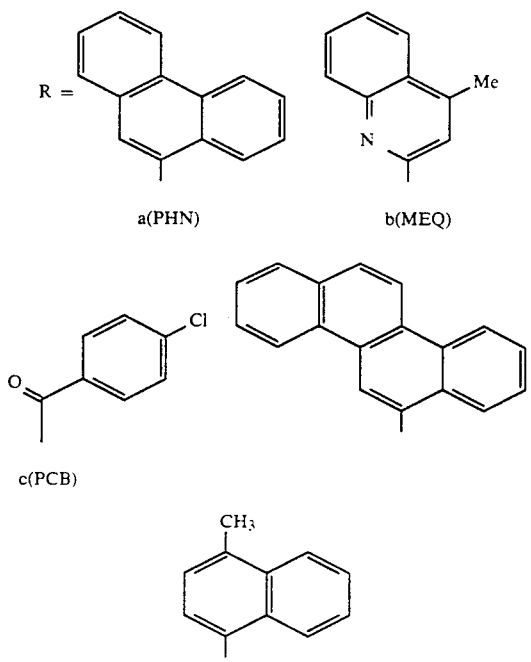

a(PHN)  b(MEQ)

c(PCB)

The R group can include other benzenoid hydrocarbons. The aromatic moieties also can be modified by substitutions such as by lower alkyl, alkoxy or halogen radical groups.

Additional effective heterocyclic aromatic ligands include:

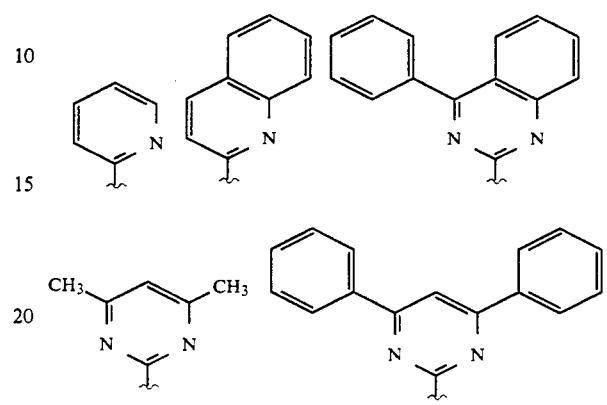

The improvements achieved with these new ligands are best appreciated through the results shown in Table 9. A particularly important advantage is that the terminal olefins (entries 1-7, Table 9), have moved into the "useful" ee-range for the first time.

TABLE 9

Ee (%)[a] of the Diols Resulting from Catalytic Asymmetric Dihydroxylation[b]

| class of olefin | entry | olefin[c] | temp. °C. | 1a(PHN) | 1b(MEQ) | 1c(PCB) | config[d] |
|---|---|---|---|---|---|---|---|
| $R^1\diagdown$ | 1 | n-C$_8$H$_{17}$ | 0 | 74 | 65 | 45[e] | R |
| | 2 | cyclo-C$_8$H$_{17}$ | 0 | 93 | 85 | 64[e] | (R) |
| | 3 | t-Bu | 0 | 79 | 79 | 44[e] | R |
| | 4 | Ph | 0 | 78 | 87 | 74[e] | R |
| | 5 | 2-naphthyl-CH=CH$_2$ | 0 | 83 | 93 | 88[e] | R |
| $R^1\diagdown\diagup R^2$ | 6 | cyclo-C$_6$H$_{11}$ | 0 | 82 | 73 | 37[e] | R |
| | 7 | 6-MeO-2-naphthyl-isopropenyl | 0 | 69 | 88 | 74[e] | (R) |
| $R^1\diagdown\diagup R^3$ | 8 | n-Bu-CH=CH-n-Bu | rt | 96 | 90 | 79 | R,R |
| | 9 | n-C$_5$H$_{11}$-CH=CH-CO$_2$Et | rt | 94 | 85 | 67 | 2S,3R |
| | 10 | Ph-CH=CH-CO$_2$Me | rt | 98 | 98 | 91 | 2S,3R |
| | 11 | Ph-CH=CH-Ph | rt | 99 | 98 | 99 | R,R |
| $R^2\diagdown\diagup R^2$ $R^2$ | 12 | Ph-C(Me)=CH$_2$ | rt | 86 | 81 | 74 | R |
| | 13 | 1-phenylcyclohexene | rt | 93 | 92 | 91 | R,R |

TABLE 9-continued

| | | | Ee (%)[a] of the Diols Resulting from Catalytic Asymmetric Dihydroxylation[b] | | | | |
|---|---|---|---|---|---|---|---|
| class of olefin | entry | olefin[c] | | temp. °C. | 1a(PHN) | 1b(MEQ) | 1c(PCB) | config[d] |

Enantiomeric excess as were determined by HPLC, GC, or $^1$H-NMR analysis of the bis-MTPA esters [7] (see supplementary materials for details of analyses). [b]All reactions were performed essentially as described in Example 20 with some variations: (1) 1-1.25 mol % OsO$_4$ or K$_2$OsO$_2$(OH); 92) 2-25 mol % ligand. (3) 0.067-0.10 M in olefin; (4) 18-24 h reaction time. In all cases the isolated yield of the diol was 75-95%. [c]All olefins are commercially available except entries 6 and 7.[8] The absolute configurations of the diols were determined by comparison of their optical rotations with literature values[9] (entries 1, 3-5, 8, 10-13), or with an authentic diol (R)-(−)-2-phenyl-1,2-propanediol (entry 6),[10] or by comparison of ORD (entry 9).[11] The remaining two (entries 2,7) are tentatively assigned by analogy from opticla rotations of closely related diols and the retention times of the bis MTPA esters on HPLC (see supplementary material for details). [d]Reaction was carried out at room temperature.

The data for the new ligands 1a and 1b has been compared to the results for another ligand, the p-chlorobenzoate 1c (last column of Table 9). Note further that the highest enantioselectivities for each substrate have been highlighted by bracketing, and that this bracketing is conspicuously sparse in the column under ligand 1c. Clearly, ligands 1a and 1b also deliver a significant ee enhancement for trans-substituted olefins, especially those lacking aromatic substitutents (entries 8 and 9).

The six possible substitution patterns for olefins are:

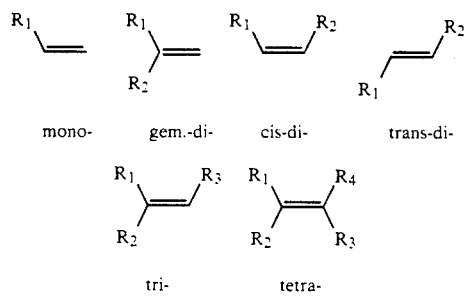

mono-  gem.-di-  cis-di-  trans-di-  tri-  tetra-

Four of these classes are represented in Table 9. The present success with the mono- and gem-disubstituted types has essentially doubled the scope of the catalytic ADH when compared to diol production when ligands other than aromatic ether ligands are used.

Strikingly absent from Table 9 are the results for the dihydroquinine ligand analogs (i.e., 2a, 2b and 2c). The quinidine and quinine analogs of these new ligands also give very good results with the same olefin classes shown in Table 9. Like the original p-chlorobenzoate ligand comparison (1c vs 2c),[2b] the quinine ether series gives somewhat lower ee's than their dihydroquinidine counterparts (1a vs 2a and 1b vs 2b). For example, vinyl cyclooctane (entry 2) gives the S-diol in 8.8% ee using 2a compared with the R-diol in 93% ee recorded in Table 9 using 1a.

The detailed general procedure for the catalytic ADH is given in note Example 20, using ligand 1a and vinyl cyclooctane as the substrate. Note the experimental simplicity of the process. I is performed in the presence of air and water at either ambient or ice bath temperature. A further advantage is that the most expensive component, the ligand, can be easily recovered in >80% yield.

Note also that the solid and nonvolatile osmium (VI) salt, K$_2$OsO$_2$(OH)$_4$, is used in place of osmium tetroxide. This innovation should be useful in all catalytic oxidations involving OsO$_4$ since it avoids the risk of exposure to volatile osmium species.

Another olefin class can be asymmetrically dihydroxylated when O-carbamoyl-,p-chlorobenzoate- or O-phenanthrolene- substitutions of DHQD or DHQ ligands are used in the method of the present invention. This class is the cis-disubstituted type of olefin. Table 10 shows the ee's and % yields for a variety of substrates when these ligands were used. Procedures for producing these ligands and for carrying out the ADH are illustrated in Examples 23 and 24.

TABLE 10

Enantiomeric Excesses (ee's) Obtained for cis-Olefins with Various Dihydroquinidine Ligands; ee (% yield)

| Substrate: Ligand: | styrene | dihydronaphthalene | cis-4-octene | tBu-vinyl | phenyl propynyl |
|---|---|---|---|---|---|
| DMC—O—DHQD | 20 (68) | 17 (71) | 4 (78) | 4 (66) | 17 (66) |
| MPC—O—DHQD | 46 (82) | 0 (54) | 6 (100) | 6 (90) | 49 (47) |
| DPC—O—DHQD | 44 (85) | 10 (37) | 0 (100) | 3 (70) | 44 (75) |
| PCB—O—DHQD | 35 (92) | 2 (80) | 19 (83) | 4 (75) | 24 (63) |
| PHN—O—DHQD | 22 ( ) | 4 (78) | 37 (89) | 7 (75) | −23 (56) |
| PhC—O—DHQD | 17 (86) | 12 (69) | 14 (84) | 0 (89) | 10 (82) | where the ligands are ether linked substituents of DHQD designated as dimethyl carbamoyl (DMC), methyl phenyl carbamoyl (MPC), diphenylcarbamoyl (DPC), p-chlorobenzoate (PCB), phenanthryl (PHN) and phenyl carbamoyl (PhC).

The greatest ee's were obtained when O-carbamoyl-DHQD ligands were employed which indicates that this class of compound is an attractive ligand for asymmetric dihydroxylation of the cis-disubstituted type of olefin. These results also demonstrate that reasonably good yields and ee's can be obtained for this olefin class and that, now, five of the six classes of olefins can successfully be asymmetrically dihydroxylated.

In general, the concentration of the chiral ligand used will range from approximately 0.001M or less to 2.0M. In one embodiment, exemplified below, the solution is 0.261M in alkaloid 1 (the dihydroquinidine derivative). In one embodiment of the method, carried out at room temperature, the concentrations of each alkaloid represented in FIG. 1 is at 0.25M. In this way, the enantiomeric excess resulting under the conditions used is maximized. The amount of chiral ligand necessary for the method of the present invention can be varied as the temperature at which the reaction occurs varies. For example, it is possible to reduce the amount of alkaloid (or other chiral ligand) used as the temperature at which the reaction is carried out is changed. For example, if it is carried out, using the dihydroquinidine derivative, at 0° C., the alkaloid concentration can be 0.15M. In another embodiment, carried out at 0° C., the alkaloid concentration was 0.0625M.

Many oxidants (i.e., essentially any source of oxygen) can be used in the present method. For example, amine oxides (e.g., trimethyl amine oxides), tert-butyl hydroperoxide, hydrogen peroxide, and oxygen plus metal catalysts (e.g., copper ($Cu^+$-$Cu^{++}$/$O_2$), platinum (Pt/$O_2$), Palladium (Pd/$O_2$) can be used. Alternatively, NaOCl, $KIO_4$, $KBrO_3$ or $KClO_3$ can be used. In one embodiment of the invention, N-methylmorpholine N-oxide (NMO) is used as the oxidant. NMO is available commercially (e.g., Aldrich Chemicals, 97% NMO anhydrous, or as a 60% solution in water). In addition, as stated above, potassium ferricyanide can be used in lieu of the amine oxide. Potassium ferricyanide is an efficient oxidant in the present method.

Osmium will generally be provided in the method of the present invention in the form of osmium tetroxide ($OsO_4$) or potassium osmate VI dihydrate, although other sources (e.g., osmium trichloride anhydrous, osmium trichloride hydrate) can be used. $OsO_4$ can be added as a solid or in solution.

The osmium catalyst used in the method of the present invention can be recycled, for re-use in subsequent reactions. This makes it possible not only to reduce the expense of the procedure, but also to recover the toxic osmium catalyst. For example, the osmium catalyst can be recycled as follows: Using reduction catalysts (e.g., Pd-C), the osmium VIII species is reduced and adsorbed onto the reduction catalyst. The resulting solid is filtered and resuspended. NMO (or an oxidant), the alkaloid and the substrate (olefin) are added, with the result that the osmium which is bound to the Pd/C solid is reoxidized to $OsO_4$ and re-enters solution and plays its usual catalytic role in formation of the desired diol. This procedure (represented below) can be carried out through several cycles, thus re-using the osmium species. The palladium or carbon can be immobilized, for example, in a fixed bed or in a cartridge.

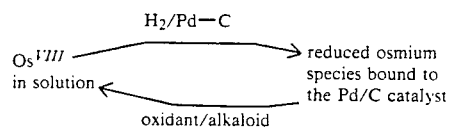

In one embodiment an olefin, such as recrystallised trans-stilbene ($C_6H_5CH$:$CHC_6H_5$), is combined with a chiral ligand (e.g., p-chlorobenzoyl hydroquinidine), acetone, water and NMO. The components can be added sequentially or simultaneously and the order in which they are combined can vary. In this embodiment, after the components are combined, the resulting combination is cooled (e.g., to approximately 0° C. in the case of trans-stilbene); cooling can be carried out using an ice-water bath. $OsO_4$ is then added (e.g., by injection), in the form of a solution of $OsO_4$ in an organic solvent (e.g., in toluene). After addition of $OsO_4$, the resulting combination is maintained under conditions appropriate for the dihydroxylation reaction to proceed.

In another preferred embodiment, a chiral ligand (e.g., dihydroquinidine 4-chlorobenzoate), NMO, acetone, water and $OsO_4$ (as a 5M toluene solution) are combined. The components can be added sequentially or simultaneously and the order in which they are combined can vary. In this embodiment, after the components are combined, the resulting combination is cooled (e.g.. to approximately 0° C.); cooling can be carried out using an ice-water bath. It is particularly preferred that the combination is agitated (e.g., stirred). To this well-stirred mixture, an olefin (e.g., trans-3-hexene) is added slowly (e.g., by injection). The optimum rate of addition (i.e., giving maximum ee), will vary depending on the nature of the olefinic substrate. In the case of trans-3-hexene, the olefin was added over a period of about 16-20 hours. After olefin addition, the mixture can be stirred for an additional period of time at the low temperature (1 hour in the case of trans-3-hexene). The slow-addition method is preferred as it results in better ee and faster reaction times.

In another embodiment, a compound which accelerates hydrolysis of the osmate ester intermediates (e.g., a soluble carboxylate salt, such as tetraethylammonium acetate) is added to the reaction mixture. The compound (approximately 1-4 equiv.) can be added to the mixture of chiral ligand, water, solvent, oxidant and osmium catalyst and olefin, or prior to the addition of olefin, if the olefin slow-addition method is used.

Figure 4:
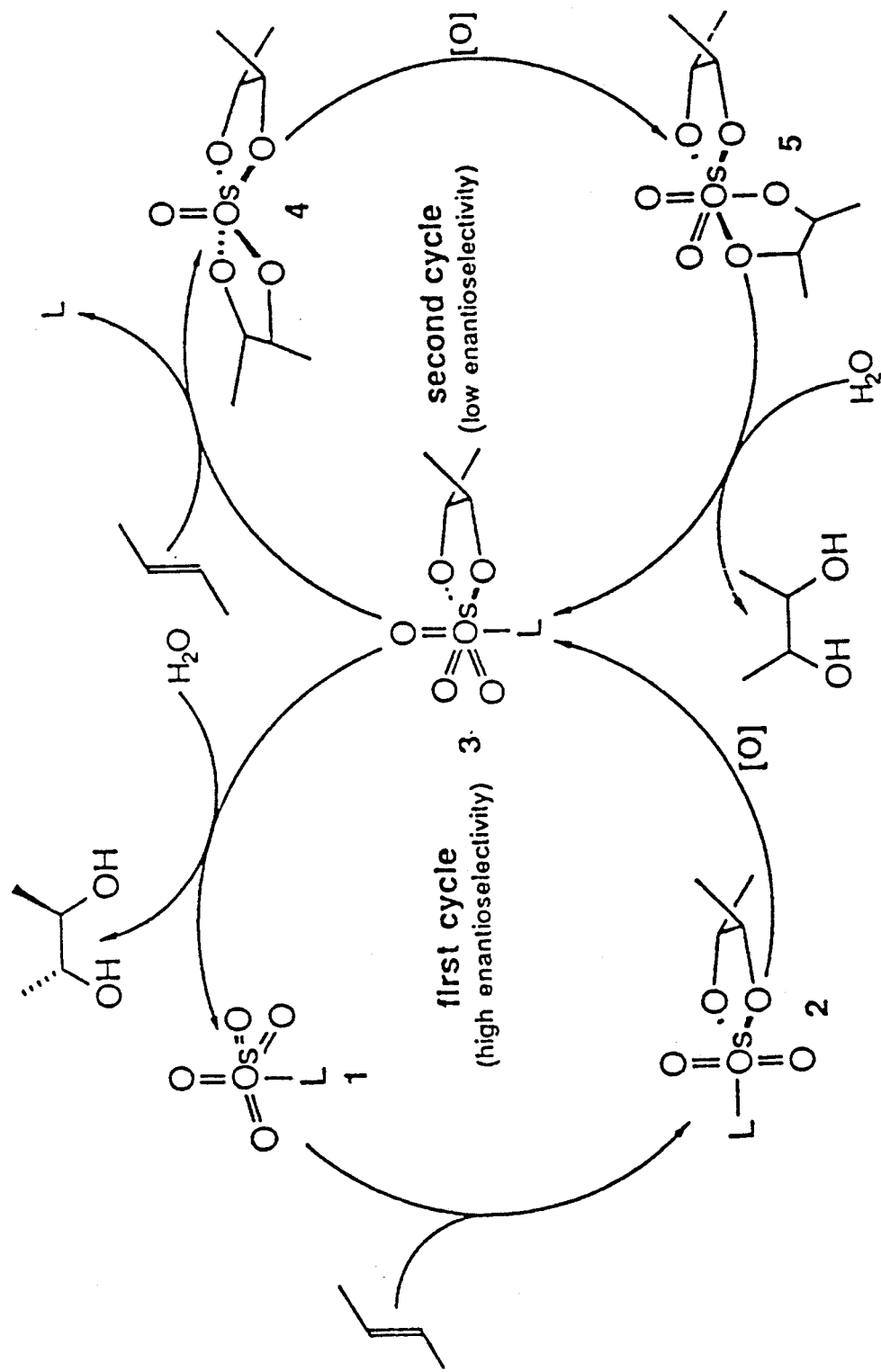
FIG. 4 is a schematic representation of a proposed mechanism of catalytic olefin dihydroxylation. This scheme shows two diol-producing cycles believed to be involved in the ligand-accelerated catalysis of the present invention. Formula 1 represents an alkaloid-osmium complex; formula 2 represents a monoglycolate ester; formula 3 represents an osmium(VIII)trioxoglycolate complex; formula 4 represents a bisglycolate osmium ester; and formula 5 represents a dioxobisglycolate.

The diol-producing mechanistic scheme which is thought to operate when the slow-addition of olefin method is used is represented in FIG. 4. According to the proposed mechanism, at least two diol-producing cycles exist. As shown in FIG. 4, only the first cycle appears to result in high ee. The key intermediate is the osmium (VIII) trioxoglycolate complex, shown as formula 3 in FIG. 4, which has the following general formula:

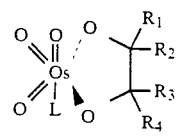

wherein L is a chiral ligand and wherein $R_1$, $R_2$, $R_3$ and $R_4$ are organic functional groups corresponding to the olefin. For example, $R_1$, $R_2$, $R_3$ and $R_4$ could be alkyl, aryl, alkoxy aryloxy or other organic functional groups compatible with the reaction process. Examples of olefins which can be used, and their functional groups, are shown on Table 4 hereinabove.

This complex occupies the pivotal position at the junction between the two cycles, and determines how diol production is divided between the cycles.

Evidence in favor of the intermediacy of the osmium (VIII) trioxoglycolate complex (formula 3, FIG. 4) is provided by the finding that the events in FIG. 4 can be replicated by performing the process in a stepwise manner under stoichiometric conditions. These experiments were performed under anhydrous conditions in toluene. In the process shown in FIG. 4, one equivalent of the alkaloid osmium complex (shown as formula 1, FIG. 4) is allowed to react with an olefin to give the emerald green monoglycolate ester (formula 2, FIG. 4). A different olefin is then added, followed by an equivalent of an anhydrous amine N-oxide, and rapid formation of the bisglycolate ester (formula 4, FIG. 4) is observed. Upon reductive hydrolysis of the bisglycolate ester, precisely one equivalent of each diol is liberated. These experiments indicate that a second cycle, presumably via the osmium trioxoglycolate complex, is as efficient as the first in producing diols from olefins. One can also use the same olefin in both steps to run this tandem addition sequence. When this was done using 1-phenylcyclohexene as the olefin, the ee for the first step was 81% and the ee for the second step was 7% in the opposite direction (i.e., in favor of the minor enantiomer in the first step). Thus, for this substrate any intrusion of the second cycle is particularly damaging, and under the original catalytic conditions 1-phenylcyclohexene only gave 8% ee (entry 3, Table 5).

Reduced ee is just part of the counterproductivity of turning on the second cycle; reduced turnover is the other liability. The bisosmate esters (formula 4, FIG. 4) are usually slow to reoxidize and hydrolyze, and therefore tend to tie up the catalyst. For example, 1-phenylcyclohexene took 7 days to reach completion under the original conditions (the 8% ee cited above). With slow addition of the olefin, the oxidation was complete in one day and gave the diol in 95% yield and 78% ee (entry 3, Table 5).

The most important prediction arising from the mechanistic scheme shown in FIG. 4 is the minimization of the second cycle if the olefin is added slowly. Slow addition of the olefin presumably gives the osmium (VIII) trioxoglycolate intermediate sufficient time to hydrolyze so that the osmium catalyst does not get trapped into the second cycle by reacting with olefin. To reiterate, the second cycle not only ruins the ee but also impedes turnover, since some of the complexes involved are slow to reoxidize and/or hydrolyze. The optimum feed rate depends on the olefin; it can be determined empirically, as described herein.

The maximum ee obtainable in the catalytic process is determined by the addition of the alkaloid osmium complex (formula 1, FIG. 4) to the olefin (i.e., the first column in Table 5). Thus, stoichiometric additions can be used to enable one to determine the ee-ceiling which can be reached or approached in the catalytic process if the hydrolysis of 3 (FIG. 4) can be made to dominate the alternative reaction with a second molecule of olefin to give 4 (FIG. 4). In the case of terminal olefins, styrene (Table 5), the trioxoglycolate esters hydrolyze rapidly, since slow addition, or the effect of the osmate ester hydrolytic additive give only a slight increase in the ee. However, most olefins benefit greatly from any modification which speeds hydrolysis of the osmate ester intermediate (3, FIG. 4) (entries 2-5, Table 5), and in extreme cases neither the effect of the osmate ester-hydrolytic additive nor slow addition is sufficient alone. Diisopropyl ethylene (entry 4, Table 5) approaches its ceiling-ee only when both effects are used in concert, with slow addition carried out in the presence of acetate. The other entries in the Table reach their optimum ee's through slow addition alone, but even in these cases the addition times can be substantially shortened if a compound, such as a tetraalkyl ammonium acetate, is present.

In many cases, temperature also affects the ee. When the ee is reduced by the second cycle, raising the temperature can often increase it. This occurs in particular, when NMO is used as the secondary oxidant. For example, diisopropyl ethylene gave 46% ee at 0° C. and 59% ee at 25° C. (24 h slow addition time in both cases). The rate of hydrolysis of the osmium trioxoglycolate intermediate is apparently more temperature dependent than the rate of its reaction with olefin. This temperature effect is easily rationalized by the expected need to dissociate the chiral ligand from the osmium complex (3) in order to ligate water and initiate hydrolysis, but the ligand need not dissociate for addition of olefin to occur (in fact this second cycle olefin addition step is also likely to be ligand-accelerated).

When $K_3Fe(CN)_6$ is used as the secondary oxidant, the effect of temperature on the ee is opposite the effect when NMO is the secondary oxidant. That is, lowering the temperature can often increase the ee when potassium ferricyanide is the secondary oxidant. Also, the olefin need not be slowly added to the mixture but can, instead, be added all at once when potassium ferricyanide is the secondary oxidant. These effects and conditions apparently occur because the second cycle is suppressed when this secondary oxidant is used. The reactions of the second cycle do not appreciably contribute to the formation of diols when the secondary oxidant is potassium ferricyanide.

The following is a description of how optimum conditions for a particular olefin can be determined. To optimize the osmium-catalyzed asymmetric dihydroxylation: 1) If from the known examples there is doubt about what the ceiling-ee is likely to be, it can be determined by performing the stoichiometric osmylation in acetone/water at 0° C. using one equivalent of the $OsO_4$—alkaloid complex; 2) Slow addition at 0° C.: the last column in Table 3 can be used as a guide for choosing the addition time, bearing in mind that at a given temperature each olefin has its own "fastest" addition rate, beyond which the ee suffers as the second cycle turns on. When the olefin addition rate is slow enough, the reaction mixture remains yellow-orange (color of 1, FIG. 4); when the rate is too fast, the solution takes on a blackish tint, indicating that the dark-brown-to-black bisglycolate complex (4, FIG. 4) is being generated; 3) If the ceiling ee is not reached after steps 1 and 2, slow addition plus tetraalkyl ammonium acetate (or other compound which assists hydrolysis of the osmate ester intermediate) at 0° C. can be used; 4) slow addition plus a soluble carboxylate salt, such as tetraalkyl ammonium acetate at room temperature can also be used. For all these variations, it is preferable that the mixtures is agitated (e.g., stirred) for the entire reaction period.

The method of the present invention can be carried out over a wide temperature range and the limits of that range will be determined, for example, by the limit of the organic solvent used. The method can be carried out, for example, in a temperature range from about 40° C. to about −30° C. Concentrations of individual reactants (e.g., chiral ligand, oxidant, etc.) can be varied as the temperature at which the method of the present invention is carried out. The saturation point (e.g., the concentration of chiral ligand at which results are maximized) is temperature-dependant. As explained previously, for example, it is possible to reduce the amount of alkaloid used when the method is carried out at lower temperatures.

The organic solvent used in the present method can be, for example, acetone, acetonitrile, THF, DME, cyclohexane, hexane, pinacolone, tert-butanol, toluene or a mixture of two or more organic solvents. These solvents are particularly suitable when NMO is the secondary oxidant.

When potassium ferricyanide ($K_3Fe(CN)_6$) is the secondary oxidant, it is advantageous to use a combination of solvents that separate into organic and aqueous phases. Although the method of the present invention can be carried out with potassium ferricyanide as the secondary oxidant using the organic solvents of the preceding paragraph, asymmetric dihydroxylation does occur but the ee's are less than when separable organic and aqueous solvent phases are employed.

The yields and ee's for a variety of organic solvents, mixed with water and a variety of substrates are shown in Tables 11–12. Table 11 shows yields and ee's for several organic solvents (with water) for a specific substrate. The ligand is either DHQD-p-chlorobenzoate (PCB) or DHQD-napthyl ether. Table 12 shows the ee's for a veriety of substrates for either t-butanol or cyclohexane as the organic phase. It is apparent from these Tables that preferred organic phase solvents include cyclohexane, hexane, ethyl ether and t-butyl methyl ether. The preferred aqueous solvent is water.

TABLE 11

Solvent Study of Catalytic ADH using $K_3Fe(CN)_6$

| Solvent | Yield (%) | ee (%) |
|---|---|---| a) Solvent Effects on Styrene Diol using DHQD-PCB Ligand
Reaction Time = 4 hours

| Cyclohexane | 83.5 | 80 |
| Hexane* | 59.9 | 76 |
| Iso-octane** | 7 | 76 |
| t-BuOH | 84.7 | 74 |
| t-Bu—O—Me | 80 | 73 |
| Toluene | 78 | 69 |
| Et$_2$O | 58.7 | 68 |
| EtOAc | 64.4 | 65 |
| THF | 61.6 | 61 |
| Chlorobenzene | 73.6 | 60 |
| CH$_3$CN | 79.0 | 50 |
| CH$_2$Cl$_2$ | 73.8 | 49 |
| DMF | 24.5 | 23 |
| MeOH | 84.1 | 5.5 | b) Solvent Effects on Hexene Diol using

TABLE 11-continued

Solvent Study of Catalytic ADH using $K_3Fe(CN)_6$

| Solvent | Yield (%) | ee (%) |
|---|---|---|

DHQD-PCB Ligand
Reaction Time = 24 hours

| Cyclohexane | 47 | 74 |
| Hexane* | 67.4 | 74 |
| t-BuOH | 84.5 | 74 |
| t-Bu—O—Me | 61.4 | 71 |
| Et$_2$O | 51.1 | 71 |
| EtOAc | 26.7 | 71 |
| Toluene | 32.4 | 69 |
| CH$_3$CN | 81.6 | 68 |
| CH$_2$Cl$_2$ | 7.6 | 67 |
| Chlorobenzene | 9.3 | 66 |
| THF | 74.1 | 65 | c) Solvent Effects on Decene Diol using DHQD-PCB Ligand
Reaction Time = 24 hours

| t-BuOH | 60.8 | 79 |
| Cyclohexane | 3.4 | 74 |
| t-Bu—O—Me | 7.6 | 71 | d) Solvent Effects on Hexene Diol using DHQD Napthyl Ether Ligand
Reaction Time = 24 hours

| t-BuOH | 49.6 | 92 |
| Cyclohexane | 36.2 | 91 |
| t-Bu—O—Me | 75.4 | 89 |
| Et$_2$O | 47.6 | 89 |
| EtOAc | 41.2 | 88 |
| Toluene | 24.6 | 87 |
| Chlorobenzene | 25.0 | 85 |
| THF | 78.6 | 83 |
| CH$_3$CN | 90.2 | 81 |
| CH$_2$Cl$_2$ | trace | 7 | e) Solvent Effect on Decene Diol using DHQD Napthyl Ether Ligand
Reaction Time = 24 hours

| t-BuOH | 40.7 | 94 |

*5 ml of t-Bu—O—Me were added to dissolve all the ligand
**6 ml of t-Bu—O—Me were added to dissolve all the ligand

TABLE 12

Ee's of Various Substrates in the Catalytic ADH $$R\overset{R'}{\diagup\!\!\!\diagdown} \xrightarrow[K_2Fe(CN)_6, K_2CO_3, Solvent/H_2O]{DHQD\text{-}PCB, cat. OsO_4, r.t.} \underset{OH}{\overset{OH}{R\diagdown\!\!\!\diagup R'}}$$

| Substrate | t-BuOH | Cyclohexane |
|---|---|---|
| styrene (PhCH=CH₂) | 73 | 80 |
| stilbene (PhCH=CHPh) | 99 | 99 |
| β-methylstyrene (PhCH=CHCH₃) | 91 | 92 |
| cinnamyl acetate (PhCH=CHCH₂OAc) | 91 | 91 |
| methyl cinnamate (PhCH=CHCO₂Me) | 91 | 93 |
| 5-decene (BuCH=CHBu) | 79 | 74 |
| 3-hexene (EtCH=CHEt) | 74 | 74 |

Figure 2:
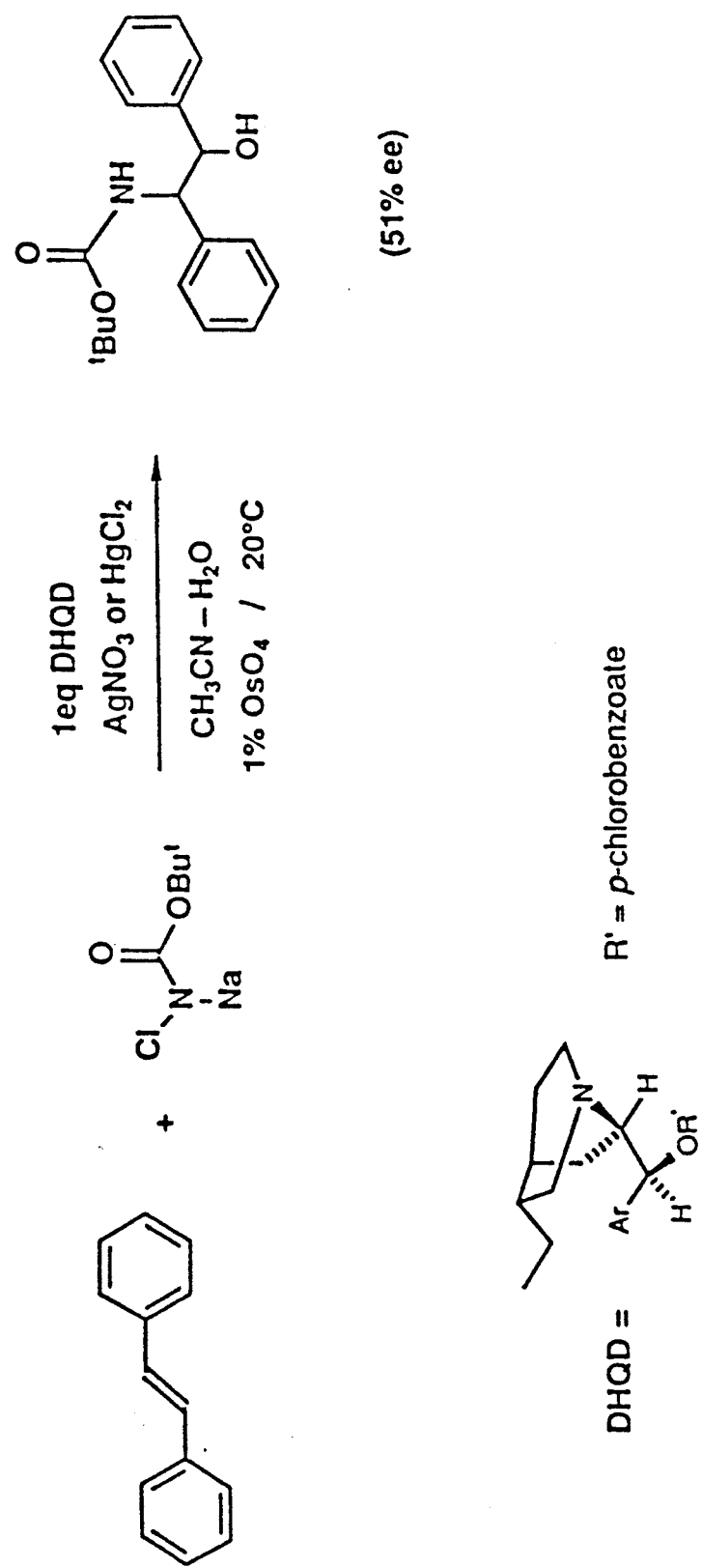
FIG. 2 is a schematic representation of asymmetric catalytic oxyamination of stilbene which is carried out by the method of the present invention.
Figure 3:
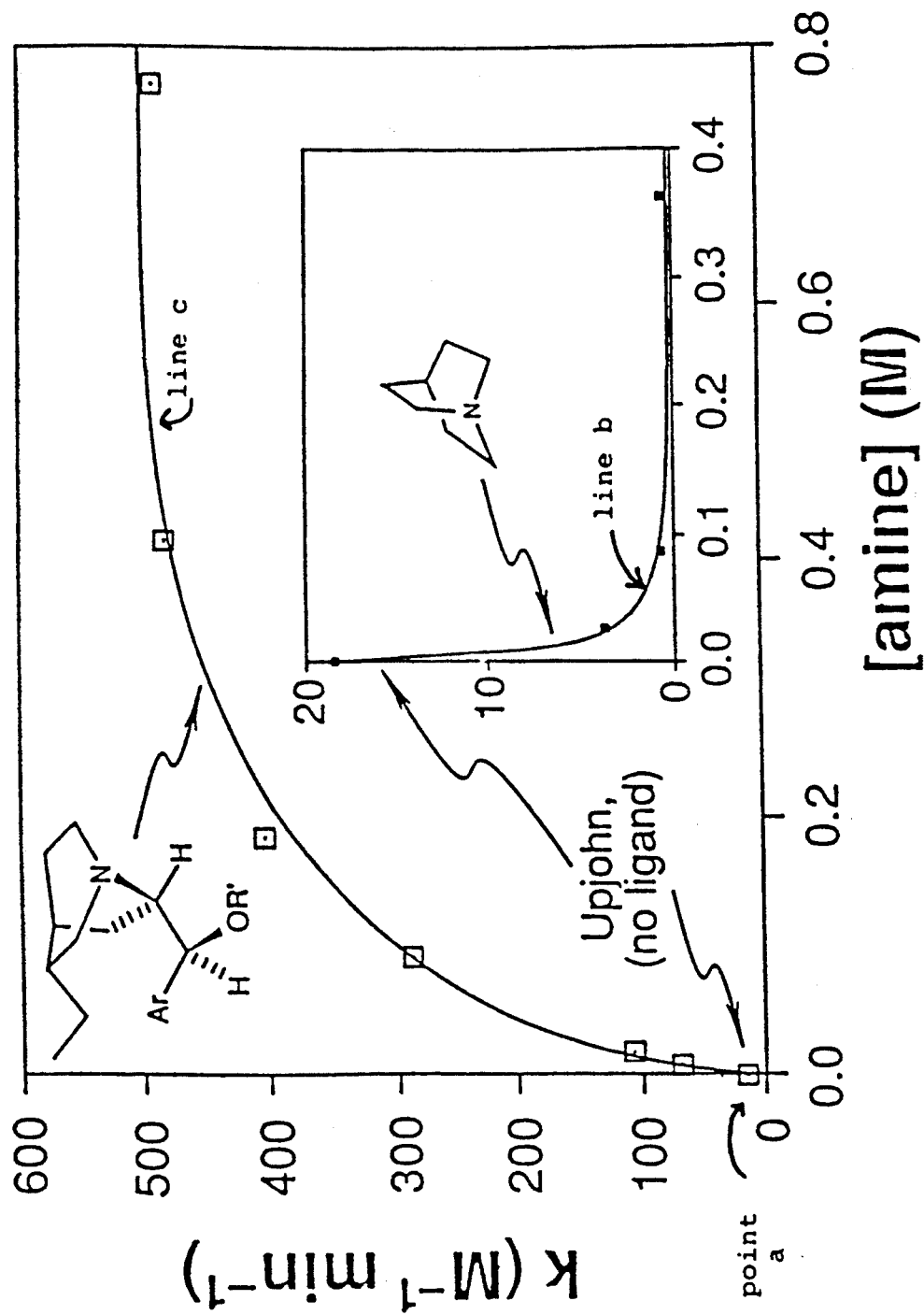
FIG. 3 is a plot of amine concentration vs second-order-rate constant k for the catalytic cis-dihydroxylation of styrene. At point a, no amine has been added. Point a thus represents the rate of the catalytic process in the absence of added amine ligands. Line b represents the rate of the catalytic process in the presence of varying amounts of quinuclidine, a ligand which substantially retards catalysis. Line c represents the rate of the catalytic process in the presence of the dihydroquinidine benzoate derivative 1 represented in FIG. 1. K is defined as $K_{obs}/[OsO_4]_o$ where rate $= -d[styrene]/dt = K_{obs}[styrene]$. Conditions: 25° C., $[OsO_4]_o = 4 \times 10^{-4}$M, $[NMO]_o = 0.2$M $[styrene]_o = 0.1$M.

In another embodiment of the present invention, styrene was combined with a chiral ligand (DHQD), acetone, water and NMO and OsO₄. The plot of amine concentration vs second-order-rate-constant K for the catalytic cis-dihydroxylation of styrene is represented in FIG. 2. The kinetic data of FIG. 2 clearly shows the dramatic effect of ligand-accelerated catalysis achieved by use of the method of the present invention. Point a in FIG. 2 represents the rate of the catalytic process in the absence of amine ligands (t½=108 minutes). Line b shows the rates of the process in the presence of varying amounts of quinuclidine, a ligand which substantially retards catalysis (at greater than 0.1M quinuclidine, t½ is greater than 30 hours). Because of the observed retarding effect of quinuclidine (ligand-decelerated catalysis) the result represented by line C was unexpected. That is, when the process occurs in the presence of dihydroquinidine benzoate derivative 1 (see FIG. 1), the alkaloid moiety strongly accelerates the catalytic process at all concentrations (with ligand 1=0.4M, t½=4.5 minutes), despite the presence of the quinuclidine moiety in its structure.

The rate of the stoichiometric reaction of styrene with osmium tetroxide and that of the corresponding catalytic process were compared. The comparison indicates that both have identical rate constants [$K_{stoic}=(5.1\pm0.1)\times10^2 M^{-1}$ min$^{-1}$ and $K_{cat}=(4.9\pm0.4)\times10^2 M^{-1}$ min$^{-1}$], and that they undergo the same rate acceleration upon addition of ligand 1. Hydrolysis and reoxidation of the reduced osmium species, steps which accomplish catalyst turnover, are not kinetically significant in the catalytic process with styrene. It may be concluded that the limiting step is the same in both processes and consists of the initial addition reaction forming the osmate ester (2, FIG. 1). A detailed mechanistic study reveals that the observed rate acceleration by added ligand 1 is due to formation of an osmium tetroxide-alkaloid complex which, in the case of styrene, is 23 times more reactive than free osmium tetroxide. The rate reaches a maximal and constant value beyond an (approximate) 0.25M concentration of ligand 1. The onset of this rate saturation corresponds to a pre-equilibrium between DHQD and osmium tetroxide with a rather weak binding constant ($K_{eq}=18\pm2 M^{-1}$). Increasing the concentration of DHQD above 0.25M does not result in corresponding increases in the enantiomeric excess of the product diol. In fact, due to the ligand-acceleration effect, the ee of the process approaches its maximum value much faster than the maximum rate is reached, which means that optimum ee can be achieved at rather low alkaloid concentrations.

At least in the case of styrene, the rate acceleration in the presence of the alkaloid is accounted for by facilitation of the initial osmylation step. The strikingly opposite effects of quinuclidine and DHQD on the catalysis can be related to the fact that although quinuclidine also accelerates the addition of osmium tetroxide to olefins, it binds too strongly to the resulting osmium(VI) ester intermediate and inhibits catalyst turnover by retarding the hydrolysis/reoxidation steps of the cycle. In contrast the alkaloid appears to achieve a balancing act which renders it near perfect for its role as an accelerator of the dihydroxylation catalysis. It binds strongly enough to accelerate addition to olefins, but not so tightly that it interferes (as does quinuclidine) with subsequent stages of the catalytic cycle. Chelating tertiary amines [e.g., 2,2'-bipyridine and (−)-(R,R)-N,N,N',N'-tetramethyl-1,2-cyclohexanediamine) at 0.2M completely inhibit the catalysis. Pyridine at 0.2M has the same effect.

As represented in Table 4, the method of the present invention has been applied to a variety of olefins. In each case, the face selection rule described above has been shown to apply (with reference to the orientation of the olefin as represented in FIG. 1). That is, in the case of the asymmetric dihydroxylation reaction in which the dihydroquinidine derivative is the chiral ligand, attack occurs on the re- or re,re- face) and in the case in which the dihydroquinine derivative is the chiral ligand, attack occurs on the si- or si,si- face. Thus, as demonstrated by the data presented in the Table 2, the method of the present invention is effective in bringing about catalytic asymmetric dihydroxylation; in all cases, the yield of the diol was 80–95%, and with the slow-addition modification, most olefins give ee's in the rage of 40–90%.

The present method can be used to synthesize chiral intermediates which are important building blocks for biologically active chiral molecules, such as drugs. In one embodiment, the present method was used to produce an optically pure intermediate used in synthesizing the drug diltiazem (also known as cardizem). The reaction is shown in the following scheme:

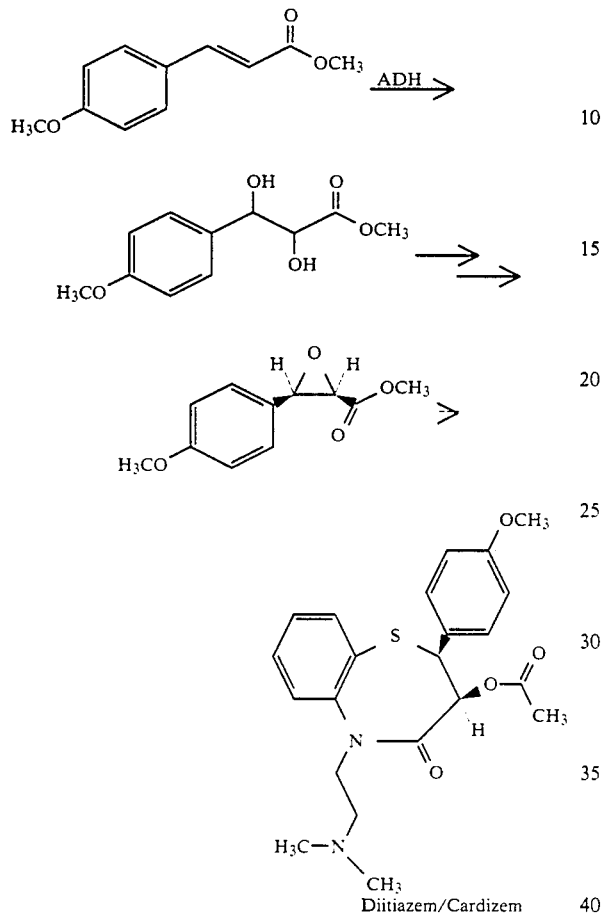

The method of the present invention is also useful to effect asymmetric vicinal oxyamination of an olefin, and may be useful for asymmetric vicinal diamination. In the case of substitution of two nitrogen or of a nitrogen and oxygen, an amino derivative is used as an amino transfer agent and as an oxidant. For example, the olefin to be modified, an organic solvent, water, a chiral ligand, an amino derivative and an osmium-containing compound are combined and the combination maintained under conditions appropriate for the reaction to occur. The amino derivative can be, for example, an N-chlorocarbamate or chloroamine T. Asymmetric catalytic oxyamination of recrystallized trans stilbene, according to the method of the present invention, is represented in FIG. 2.

In another embodiment, the present method was used to produce intermediates for the synthesis of homo-brassinolide and 24-epibrassinolide, which are known to exhibit the same biological activities as brassinolide. These brassinosteroids show very potent plant-growth activity at hormonal level and access to these compounds in a large quantity can only be achieved by synthetic means.

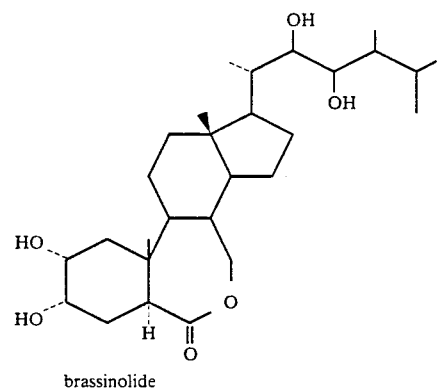
brassinolide

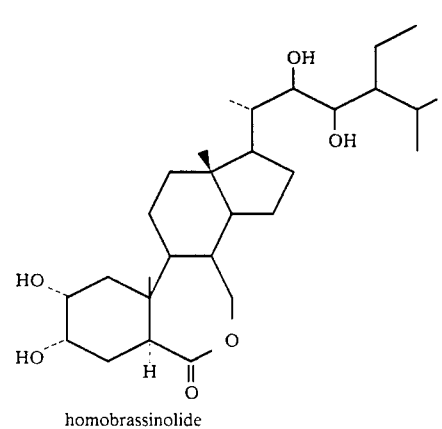
homobrassinolide

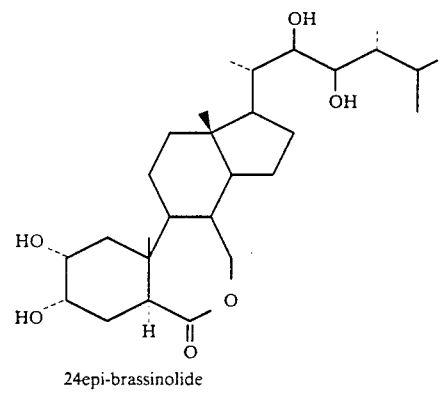
24epi-brassinolide

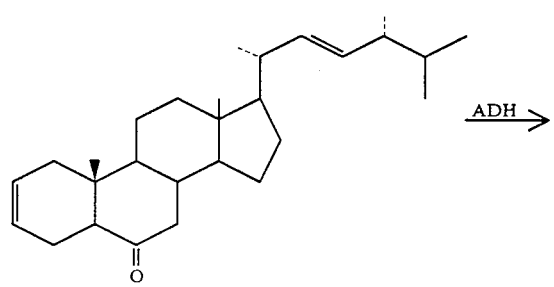

-continued

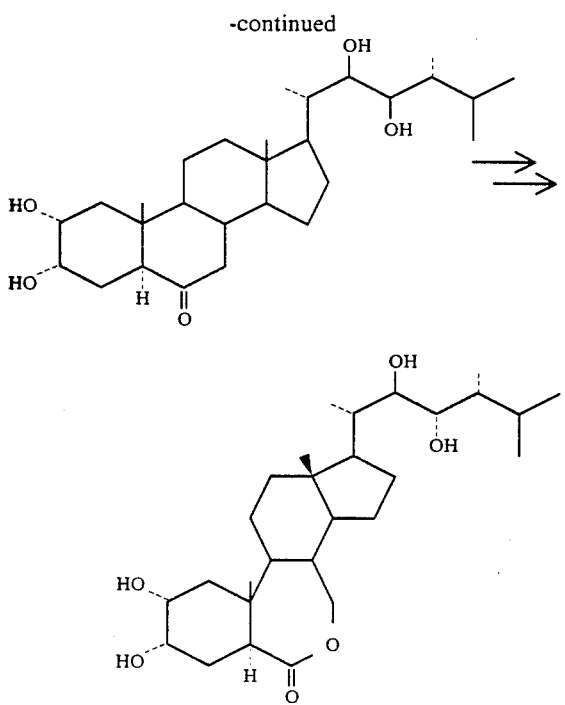

In another embodiment of the present method, highly optically active diol was produced from the asymmetric dihydroxylation of ethyl trans-2-octenoate. This diol has been converted to optically pure β-lactam structure, which are well-known for their antibiotic activities:

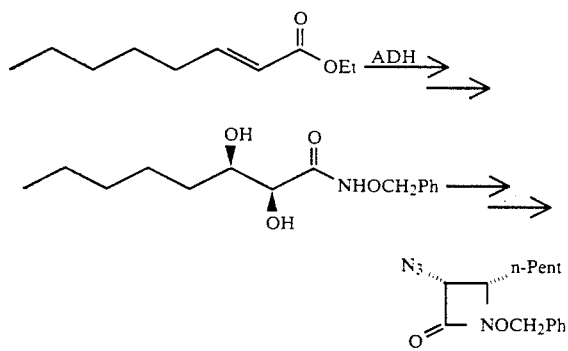

An embodiment of the present invention pertains to compositions that are useful as chiral ligands in asymmetric dihydroxylation reactions. These compositions can be envisioned as being composed of three parts.

One part of the compositions is an alkaloid or alkaloid derivative. Examples of such alkaloids are the cinchona alkaloids. Quinidine, dihydroquinidine, quinine and dihydroquinine are particularly exemplary members of these alkaloids.

The second part of the compositions of the present invention is an organic group or substituent of moderate size. This organic substituent is relatively bulky and often has a molecular weight in excess of 300 daltons. The atomic constituents of this organic substituent usually are carbon, hydrogen, oxygen and nitrogen but can be any type including phosphorus and sulfur. The organic substituent can be aromatic or nonaromatic, heterocyclic or nonheterocyclic or can contain combinations of subsidiary organic groups. The organic substituent often occupies space in three dimensions rather than be linear or planar although the latter configurations can be used. Preferred embodiments of the organic substituent are alkaloids or alkaloid derivatives. Again, cinchona alkaloids such as quinidine, dihydroquinidine, quinine and dihydroquinine can be utilized. When these cinchona alkaloids are used, the composition of the present invention contains two cinchona alkaloids. In many instances the two cinchona alkaloids are identical. In those instances of incorporation of two alkaloids or alkaloid derivatives of similar or the same configuration in the composition of the invention, the composition has symmetry attributes that do not occur when the organic substituent is not an alkaloid or alkaloid derivative. It is not essential in this embodiment of the invention for the composition to contain two alkaloids or alkaloid derivatives, but when two alkaloid moieties are present, the composition has a somewhat different character than when one alkaloid moiety is present. When two alkaloids or alkaloid derivatives are incorporated in the composition of the invention, either one can participate in the reaction scheme as represented in FIG. 1. This attribute of the composition is particularly beneficial when the two alkaloids or alkaloid derivatives are identical because they participate in the reaction scheme in the same manner, as illustrated in FIG. 1.

The third part of the compositions of the present invention is a spacer group that resides between the alkaloid or alkaloid derivative and the organic substituent. This spacer group links the alkaloid or alkaloid derivative and the organic substituent through covalent bonds between these two constituents and the spacer group. That is, the spacer group is covalently linked to the alkaloid or alkaloid derivative and to the organic substituent which can be another alkaloid or alkaloid derivative. When the alkaloid or alkaloid derivative (and the organic substituent when it is an alkaloid or alkaloid derivative) is a cinchona alkaloid, such as dihydroquinidine, quinidine, dihydroquinine or quinine, the covalent bond is usually an ether linkage at the 9'-oxygen of the cinchona alkaloid.

The spacer group is a planar aromatic hydrocarbon. Often, the planar aromatic hydrocarbon consists of one or more aromatic ring structures but this attribute is not required. When ring structures form the aromatic spacer group they can be heterocyclic. Nitrogen heterocyclics are particularly preferred. Examples of such planar aromatic spacer groups are benzene, napthalene, pyridazine, pyrimidine, pyrazine, s-triazine, phthalazine, quinazoline, quinoxaline, napthyridine, pyrido[3,2-b]-pyridine, acridine, phenazine and halogen or alkyl substituted derivatives of these compounds. In preferred embodiments of the invention, pyridazine or phthalazine are the spacer groups.

Compositions of this invention, therefore, are alkaloids, such as cinchona alkaloids, or alkaloid derivatives covalently linked to planar aromatic spacer groups which, in turn, are covalently linked to organic substituents whose molecular weight is at least 300 daltons. These organic substituents often are alkaloids, such as cinchona alkaloids, or alkaloid derivatives. In many instances, the organic substituents are identical to the alkaloids or alkaloid derivatives that are also covalently linked to the spacer group. In these instances, the compositions of the present invention are two identical alkaloids, such as cinchona alkaloids, or alkaloid derivatives covalently linked to each other through a planar aromatic spacer group. Particularly preferred embodiments of this aspect of the present invention are phthalazine or pyridazine which are disubstituted with either dihydroquinidine, quinidine, dihydroquinine or quinine. These embodiments are 1,4-bis-(9'-O-dihydroquinidyl)-phthalazine, 1,4-bis-(9'-O-quinidyl)-phthalazine, 3,6-bis-(9'-O-dihydroquinidyl)-pyridazine, 3,6-bis-(9'-O-quinidyl)-pyridazine, 1,4-bis-(9'-O-dihydroquinyl)-phthalazine, 1,4-bis-(9'-O-quinyl)-phthalazine, 3,6-bis-(9'-O-dihydroquinyl)-pyridazine and 3,6-bis-(9'-O-quinyl)-pyridazine.

Another embodiment of the present invention pertains to methods for asymmetric dihydroxylation of olefins using the compositions just described in the immediately preceding paragraphs as the chiral ligands in the asymmetric dihydroxylation reaction. In these methods, the chiral ligands that are alkaloids or alkaloid derivatives covalently linked to planar aromatic spacer groups which, in turn, are covalently linked to organic substituents whose molecular weight is at least 300 daltons are called chiral auxiliaries. A chiral auxiliary, an organic solvent, an aqueous solution, a base, a ferricyanide salt and an osmium-containing catalyst are combined as previously described. The olefin can be present as this combination is being formed or it can be added after the listed combination has been made. The resulting combination is maintained, as previously described, under conditions that allow asymmetric addition to the olefin to occur. The difference between the methods of the present embodiment and previously described methods of other embodiments is the chiral ligand (here the chiral auxiliary) that is used in the asymmetric dihydroxylation reaction.

In preferred embodiments of these methods of the present invention, the alkaloids of the chiral auxiliary are cinchona alkaloids such as dihydroquinidine, quinidine, dihydroquinine and quinine. In further preferred embodiments of these methods, the organic substituents are alkaloids, such as cinchona alkaloids, or alkaloid derivatives. In still further preferred embodiments of these methods, the planar aromatic spacer group is a nitrogen heterocyclic such as pyridazine or phthalazine. In particularly preferred embodiments of these methods, the chiral auxiliary is a bis-(cinchona alkaloid)-pyridazine or bis-(cinchona alkaloid)-phthalazine listed above.

In these methods of the present invention, a ferricyanide salt is used as the secondary oxidant. The important moiety of the salt is the ferricyanide anion. The specific cation of the salt is not critical and can be, for example, potassium, sodium, calcium, magnesium or an organic cation. In particular embodiments of these methods, potassium ferricyanide is the chosen salt.

These methods of the present invention, using the chiral auxiliaries, produce asymmetrically dihydroxylated olefins with better ee values than when previously described chiral ligands are used. This is particularly evident for 1,2-diols synthesized from terminal mono- and 1,1-disubstituted olefins in a temperature range from 0° C. to 25° C. This feature is shown in Table 16 of Example 26.

In addition, in these methods of the present invention a small amount of chiral auxiliary is all that is needed to produce asymmetrically dihydroxylated olefins with good yields and ee values. This is shown in Table 17 of Example 26.

EXAMPLE 1

Asymmetric Dihydroxylation of Stilbene

The following were placed sequentially in a 2 L bottle (or flask): 180.2 g (1.0M) of recrystallised trans stilbene (Aldrich 96%), 62.4 g (0.134 moles; 0.134 eq) of the p-chlorobenzoate of hydroquinidine (1), 450 mL of acetone, 86 mL of water (the solution is 0.261M in alkaloid 1) and 187.2 g (1.6 mol, 1.6 eq.) of solid N-Methylmorpholine N-Oxide (NMO, Aldrich 97%). The bottle was capped, shaken for 30 seconds, cooled to 0°-4° C. using an ice-water bath. $OsO_4$ (4.25 mL of a solution prepared using 0.120 g $OsO_4$/mL toluene; 0.002 Mol %; 0.002 eq.) was injected. The bottle was shaken and placed in a refrigerator at ca. 4° C. with occasional shaking. A dark purple color developed and was slowly replaced by a deep orange one; the heterogeneous reaction mixture gradually became homogeneous and at the end of the reaction, a clear orange solution was obtained. The reaction can be conveniently monitored by TLC (silica gel; $CH_2Cl_2$; disappearance of the starting material at a defined Rf). After 17 hours, 100 g of solid sodium metabisulfite ($Na_2S_2O_5$) were added, the reaction mixture was shaken (1 minute) and left at 20° C. during 15 minutes. The reaction mixture was then diluted by an equal volume of $CH_2Cl_2$ and anhydrous $Na_2SO_4$ added (100 g). After another 15 minutes, the solids were removed by filtration through a pad of celite, washed three times with 250 mL portions of $CH_2Cl_2$ and the solvent was evaporated under vacuum (rotatory-evaporator, bath temperature=30°-35° C.).

The crude oil was dissolved in ethyl acetate (750 mL), extracted three times with 500 ml. portions of 2.0M HCl, once with 2.0M NaOH, dried over $Na_2SO_4$ and concentrated in vacuo to leave 190 g (89%) of the crude diol as a pale yellow solid. The enantiomeric excess of the crude R,R-diol was determined to be 78% by HPLC analysis of the derived bis-acetate (Pirkle 1A column using 5% isopropanol/hexane mixture as eluant. Retention times are: t1=18.9 minutes; t2=19.7 minutes. Recrystallization from about 1000 ml. $CH_2Cl_2$ gave 150 g (70%) of pure diol (ee=90%). A second recrystallization gave 115 g of diol (55% yield) of 99% ee. Ee (enantiomeric excess) is calculated from the relationship (for the R enantiomer, for example): percent $$e.e. = [(R)-(S)/[(R)+(S)] \times 100.$$

The aqueous layer was cooled to 0° C. and treated with 2.0M NaOH (about 500 mL) until pH=7. Methylene chloride was added (500 mL) and the pH adjusted to 10-11 using more 2.0M NaOH (about 500 mL). The aqueous layer was separated, extracted twice with methylene chloride (2×300 mL) and the combined organic layers were dried over $Na_2SO_4$. The solvent was removed in vacuo to provide the alkaloid as a yellow foam. The crude alkaloid was dissolved in ether (1000 mL), cooled to 0° C. (ice-bath) and treated with dry HCl until acidic pH (about 1-2). The faint yellow precipitate of p-chlorobenzoylhydroquinidine hydrochloride was collected by filtration and dried under high vacuum (0.01 mm Hg).

The free base was liberated by suspending the salt in ethyl acetate (500 mL), cooling to 0° C. and adding 28% $NH_4OH$ until pH=11 was reached. After separation, the aqueous layer was extracted twice with ethyl acetate, the combined organic layers were dried over $Na_2$-

$SO_4$ and the solvent removed in vacuo to give the free base as a white foam.

EXAMPLE 2

Asymmetric Dihydroxylation of Stilbene

To a 3 L, 3-necked round-bottomed flask equipped with a mechanical stirrer and two glass stoppers at room temperature were added E-1,2-diphenylethene (Trans-stilbene) (180.25 g, 1.0 mol, 1.0 eq), 4-methylmorpholine N-oxide (260 mL of a 60% by wt. aqueous solution (1.5 mol, 1.5 eq) dihydroquinidine 4-chlorobenzoate (23.25 g, 0.05 mol, 0.05 eq) 375 mL acetone and 7.5 mL $H_2O$. The solution was 0.1M in alkaloid M in olefin, and the solvent was 25% water/75% acetone (v/v). The flask was immersed in a 0° C. cooling bath and stirred for 1 h. Osmium tetroxide (1.0 g, 4.0 mmol., $4.0 \times 10^{-3}$ eq) was added in one portion producing a milky brown-yellow suspension. The reaction mixture was then stirred at 0° C. for 24 h and monitored by silica TLC (3:1 $CH_2Cl_2:Et_2O$ v/v). At this point, sodium metabisulfite (285 g, 1.5 mol) was added, the mixture was diluted with 500 mL of $CH_2Cl_2$, warmed to room temperature, and stirred at room temperature for 1 h. Anhydrous sodium sulfate (50 g) was added and the mixture was stirred at room temperature overnight. The suspension was filtered through a 20 cm Buchner funnel, the filtrand was rinsed thoroughly with acetone (3×250 mL), and the filtrate was concentrated to a brown paste on a rotary evaporator with slight heating (bath temperature 30°-40° C). The paste was dissolved in 3.5 L of EtOAc, transferred to a 6 L separatory funnel and washed sequentially with $H_2O$ (2×500 mL), and brine (1×500 mL). The initial aqueous washes were kept separate from the subsequent acid washes which were retained for alkaloid recovery. The organic layer was dried ($Na_2SO_4$), and concentrated to give the crude diol in quantitative yield (222.7 g, 1.04 mol, 104%). The ee of the crude product was determined by $^1H$ NMR analysis of the derived bis-Mosher ester to be 90%. One recrystallization from hot 95% aqueous ethanol (3 mL/g) afforded 172-180 g (80-84%) of enantiomerically pure stilbene diol as a white solid, mp 145.5°-146.5° C., $[\alpha]_D^{25}=91.1°$ (c=1.209, abs EtOH).

EXAMPLE 3

Asymmetric Dihydroxylation of Stilbene

Asymmetric dihydroxylation of stilbene was carried out as described in Example 1, except that 1.2 equivalents of NMO were used.

EXAMPLE 4

Asymmetric Dihydroxylation of Stilbene

Asymmetric dihydroxylation of stilbene was carried out as described in Example 1, except that 1.2 equivalents of NMO, as a 62% wt. solution in water, were used.

EXAMPLE 5

Preparation of dihydroquinidine derivative

Preparation of dihydroquinidine by catalytic reduction of quinidine

To a solution of 16.2 g of quinidine (0.05 mol) in 150 mL of 10% $H_2SO_4$ (15 g conc $H_2SO_4$ in 150 mL $H_2O$) was added 0.2 g of $PdCl_2$ (0.022 eq; 0.0011 mol). The reaction mixture was hydrogenated in a Parr shaker at 50 psi pressure. After 2 h, the catalyst was removed by filtration through a pad of celite and washed with 150 mL of water. The faint yellow solution so obtained was slowly added to a stirred aqueous NaOH solution (15 g of NaOH in 150 mL $H_2O$. A white precipitate immediately formed and the pH of the solution was brought to 10-11 by addition of excess aqueous 15% NaOH. The precipitate was collected by filtration, pressed dry and suspended in ethanol (175 mL). The boiling solution was quickly filtered and upon cooling to room temperature, white needles crystallized out. The crystals were collected and dried under vacuum (90° C.; 0.05 mm Hg) overnight. This gave 8.6 g (52.7%) of pure dihydroquinidine mp=169.5°-170° C. The mother liquor was placed in a freezer at −15° C. overnight. After filtration and drying of the crystals, another 4.2 g (21.4%) of pure material was obtained, raising the total amount of dihydroquinidine to 12.8 g (74.1%).

Preparation of dihydroquinidine p-chlorobenzoate (ligand 1)

From dihydroquinidine hydrochloride (Aldrich)

To cooled (0° C.) suspension of 100 g dihydroquinidine hydrochloride (0.275 mol) in 300 mL of dry $CH_2Cl_2$ was added, over 30 minutes with efficient stirring, 115 mL of $Et_3N$ (0.826 eq; 3 eqs) dissolved in 50 mL of $CH_2Cl_2$. The dropping funnel was rinsed with an additional 20 mL of $CH_2Cl_2$. After stirring 30 minutes at 0° C., 42 mL of p-chlorobenzoyl chloride (0.33 mol;57.8 g; 1.2 eq) dissolved in 120 mL of $CH_2Cl_2$ was added dropwise over a period of 2 h. The heterogeneous reaction mixture was then stirred 30 minutes at 0° C. and 1 hour at room temperature; 700 mL of a 3.0M NaOH solution was then slowly added until pH=10-11 was obtained. After partitioning, the aqueous layer was extracted with three 100 mL portions of $CH_2Cl_2$. The combined organic layers were dried over $Na_2SO_4$ and the solvent removed in vacuo (rotatory evaporator). The crude oil was dissolved in 1 L of ether, cooled to 0° C. and treated with HCl gas until the ether solution gives a pH of about 2 using wet pH paper. The slightly yellow precipitate was collected and dried under vacuum to give 126 g (91.5%) of dihydroquinidine p-chlorobenzoate hydrochloride.

The salt was suspended in 500 mL of ethyl acetate, cooled to 0° C. and treated with 28% $NH_4OH$ until pH=11 was reached. After separation, the aqueous layer was extracted with two 200 mL portions of ethyl acetate. The combined organic layers were dried over $Na_2SO_4$ and the solvent removed under vacuum, leaving the free base 1 as a white foam (112 g; 88% overall). This material can be used without further purification, or it can be recrystallized from a minimum volume of hot acetonitrile to give an approximately 70-80% recovery of colorless crystals: mp: 102°-104° C., []$^{25}$D-76.5° [c1.11, EtOH); IR ($CH_2Cl_2$) 2940, 2860, 1720, 1620, 1595, 1520, 1115, 1105, 1095, 1020 $cm^{-1}$; $^1H$ NMR ($CDCl_3$) 8.72 (d, 1H, J=5Hz), 8.05 (br d, 3H, J=9.7Hz), 7.4 (m, 5H), 6.72 (d, 1H, J=7.2Hz), 3.97 (s, 3H), 3.42 (dd, 1H, J=9, 19.5Hz), 2.9-2.7 (m, 4H), 1.87 (m, 1H), 1.75 (br s, 1H), 1.6-1.45 (m, 6H), 0.92 (t, 3H, J=7Hz). Anal. Calcd for $C_{27}H_{29}ClN_2O_3$: C, 69.74; H, 6.28; Cl, 7.62; N, 6.02. Found: C, 69.95;H, 6.23; Cl, 7.81; N, 5.95.

From dihydroquinidine

To a 0° C. solution of 1.22 g dihydroquinidine (0.0037 mol) in 30 mL of $CH_2Cl_2$ was added 0.78 mL of $Et_3N$ (0.0056 mol; 1.5 eq), followed by 0.71 mL of p-chlorobenzoyl chloride (0.005 mol; 1.2 eq) in 1 mL $CH_2Cl_2$. After stirring 30 minutes at 0° C. and 1 hour at room temperature, the reaction was quenched by the addition of 10% $Na_2CO_3$ (20 mL). After separation, the aqueous layer was extracted with three 10 mL portions of $CH_2Cl_2$. The combined organic layers were dried over $Na_2SO_4$ and the solvent removed under vacuum. The crude product was purified as described above. Dihydroquinidine p-chlorobenzoate (1) was obtained in 91% yield (1.5 g) as a white foam.

Recovery of dihydroquinidine p-chlorobenzoate

The aqueous acidic extracts (see EXAMPLE 1) were combined, cooled to 0° C. and treated with 2.0M NaOH solution (500 mL) until pH=7 was obtained. Methylene chloride was added (500 mL) and the pH was adjusted to 10-11 using more 2.0M NaOH. The aqueous layer was separated and extracted with two 300 mL portions of $CH_2Cl_2$. The combined organic layers were dried over $Na_2SO_4$ and concentrated to leave the crude alkaloid as a yellow foam. The crude dihydroquinidine p-chlorobenzoate (1) was dissolved in 1 L of ether, cooled to 0° C. and HCl gas was bubbled into the solution until a pH of 1-2 was obtained using wet pH paper. The pale yellow precipitate of 1 as the hydrochloride salt was collected by filtration and dried under high vacuum (0.01 mm Hg). The free base was liberated by suspending the salt in 500 mL of ethyl acetate, cooling the heterogeneous mixture to 0° C. and adding 28% $NH_4OH$ (or 15% NaOH) until pH=11 was obtained. After separation, the aqueous layer was extracted with two 100 mL portions of ethyl acetate, the combined organic layers were dried over $Na_2SO_4$ and the solvent removed in vacuo to give 56 g (91% recovery) of pure dihydroquinidine p-chlorobenzoate (1) as a white foam.

EXAMPLE 6

Preparation of dihydroquinine derivative

Preparation of dihydroquinine p-chlorobenzoate

The catalytic hydrogenation and p-chlorobenzoylation were conducted as described for the dihydroquinidine p-chlorobenzoate to give a white amorphous solid in 85-90% yield. This solid can be used without further purification, or it can be recrystallized from a minimum volume of hot acetonitrile to afford colorless crystals: Mp:130°-133° C., $[\alpha]^{25}D+150°$ (c 1.0, EtOH). The physical properties of the solid before recrystallization (i.e., the "white amorphous solid") are as follows: $[]^{25}D+142.1$ (C=1, EtOH); IR ($CH_2Cl_2$) 2940, 2860, 1720, 1620, 1595, 1508, 1115, 1105, 1095, 1020 $cm^{-1}$, $^1H$ NMR ($CDCl_3$)d 8.72 (d, 1H, J=5Hz), 8.05 (br d, 3H, J=8Hz), 7.4 (m, 5H), 6.7 (d, 1H, J=8Hz), 4.0 (s, 3H), 3.48 (dd, 1H, J=8.5, 15.8Hz), 3.19 (m, 1H), 3.08 (dd, 1H, J=11, 15Hz), 2.69 (ddd, 1H, J=5, 12, 15.8Hz), 2.4 (dt, 1H, J=2.4, 15.8Hz), 1.85-1.3 (m, 8H), 0.87 (t, 3H, J=Hz). Anal. Calcd for $C_{27}H_{29}ClN_2O_3$: C, 69.74; H, 6.28; Cl, 7.62; N, 6.02. Found: C, 69.85; H, 6.42; Cl, 7.82; N, 5.98.

Recovery of dihydroquinine p-chlorobenzoate (2)

The procedure is identical to that described above for recovery of 1.

EXAMPLE 7

Procedure for Asymmetric Dihydroxylation of Trans-3-hexene Under "Slow Addition" Conditions To a well stirred mixture of 0.465 g (1 mmol, 0.25 eq=0.25M in L) dihydroquinidine 4-chlorobenzoate (Aldrich, 98%), 0.7 g (6 mmol, 1.5 eq) N-methylmorpholine N-oxide (Aldrich, 97%), and 32 L of a 0.5M toluene solution of osmium tetroxide (16 mol, $4 \times 10^{-3}$ equiv), in 4 mL of an acetone-water mixture (10:1 v/v) at 0° C., neat 0.5 mL (0.34 g, 4 mmol) trans-3-hexene (Wiley, 99.9%) was added slowly, via a gas tight syringe controlled by a syringe pump and with the tip of the syringe needle immersed in the reaction mixture, over a period of 16 h. The mixture gradually changed from heterogeneous to homogeneous. After the addition was complete, the resulting clear orange solution was stirred at 0° C. for an additional hour. Solid sodium metabisulfite ($Na_2S_2O_5$, 1.2 g) was added and the mixture was stirred for 5 min, and then diluted with dichloromethane (8 mL) and dried ($Na_2SO_4$). The solids were removed by filtration, and washed three times with dichloromethane. The combined filtrates were concentrated, and the residual oil was subjected to flash column chromatography on silica gel (25 g, elution with diethyl ether-dichloromethane, 2:3 v/v, $R_f$ 0.33) and collection of the appropriate fractions afforded 0.30-0.32 g (85-92% yield) of the hexanediol. The enantiomeric excess of the diol was determined by GLC analysis (5% phenyl-methylsilicone, 0.25 m film, 0317 mm diameter, 29 m long) of the derived bis-Mosher ester to be 70%.

When the above reaction was repeated with 1.2 mL (6 mmol, 1.5 eq) 60% aqueous NMO (Aldrich) in 4 mL acetone, an ee of 71% was obtained. Thus, this aqueous NMO gives equivalent results and is almost twenty times less expensive than the 97% solid grade. With an alkaloid concentration of only 0.1M (i.e., 0.186 g) and with an olefin addition period of 20 hours at 0° C., the ee was 65%. A small sacrifice in ee thus leads to a large saving in alkaloid. At 0° C., both trans-3-hexene and trans- -methylstyrene reach their maximum ee value between 0.20 and 0.25M alkaloid concentration.

EXAMPLE 8

Asymmetric Dihydroxylation of 1-Phenylcyclohexene with $Et_4NOAc-4H_2O$

The procedure set out in Example 1 was followed, except that 1-phenylcyclohexene (1.0M) was substituted for trans-stilbene. The reaction was allowed to proceed for three days, after which only 40% conversion to the diol was obtained (8% ee).

The above procedure was repeated, with the difference that 2 equivalents of tetraethyl ammonium acetate ($Et_4NOAc-4H_2O$) was added to the reaction mixture at the beginning of the reaction. Fifty-two (52%) percent ee was obtained using this procedure, and the reaction was finished in about one day.

EXAMPLE 9

Asymmetric Dihydroxylation of trans-Stilbene under "phase-transfer" conditions in toluene To a well-stirred mixture of 58.2 mg (0.125 mmol; 0.25 eq.) of the p-chlorobenzoate of hydroquinidine, 1 mL of toluene, 88 mg (0.75 mmol; 1.5 eq.) of N-methylmorpholine N-oxide, 181 mg (1 mmol; 2 eq.) of tetramethylammonium hydroxide pentahydrate, 57 μL (2 mmol; 2 eq.) of acetic acid, 0.1 mL of water, and $OsO_4$ (4.2 μL of solution prepared using 121 mg $OsO_4$/mL toluene; 0.004 Mol %, 0.004 eq.) at room temperature, a toluene solution (1 mL) of 90 mg (0.4 mmol) of trans-stilbene was added slowly, with a gas-tight syringe controlled by a syringe pump and with the tip of the syringe needle immersed in the reaction mixture, over a period of 24 h. After the addition was completed, 10% NaHSO$_3$ solution (2.5 mL) was added to the mixture, and the resulting mixture was stirred for 1 h. Organic materials were extracted with ethyl acetate, and the combined extracts were washed with brine and dried over Na$_2$SO$_4$. The solvent was evaporated under reduced pressure, and the residual oil was subjected to column chromatography on silica gel (5 g, elution with hexane-ethyl acetate, 2:1 v/v, R$_f$0.17) to afford 67.3 mg (63%) of the diol. The enantiomeric excess of the diol was determined by HPLC analysis of the derived bis-acetate (Pirkle 1A column using 5% isopropanol/hexane mixture as eluant. Retention times are: t$_1$=22.6 minutes; t$_2$=23.4 minutes) to be 94%.

EXAMPLE 10

Asymmetric Dihydroxylation of trans-Methyl 4-methoxycinnamate under phase-transfer conditions in toluene To a well-stirred mixture of 116.3 mg (0.25 eq.) of the p-chlorobenzoate of hydroquinidine, 2 mL of toluene, 175.8 mg (1.5 mmol; 1.5 eq.) of N-methylmorpholine N-oxide, 522 mg (2 mmol; 2 eq.) of tetraethylammonium acetate tetrahydrate, 0.2 mL of water, and OsO$_4$ (8.4 µL of solution prepared using 121 mg OsO$_4$/mL toluene; 0.004 Mol %, 0.004 eq.) at room temperature, a toluene solution (1 mL) of 192 mg (1 mmol) of trans-methyl 4-methoxycinnamate was added slowly, with a gas-tight syringe controlled by a syringe pump and with the tip of the syringe needle immersed in the reaction mixture, over a period of 24 h. After the addition was complete, 10% NaHSO$_3$ solution (5 mL) was added to the mixture, and the resulting mixture was stirred for 1 h. Organic materials were extracted with ethyl acetate, and the combined extracts were washed with brine and dried over Na$_2$SO$_4$. The solvent was evaporated under reduced pressure, and the residual oil was subjected to column chromatography on silica gel (10 g, elution with hexane-ethyl acetate, 2:1 v/v R$_f$0.09) to afford 118.8 mg (53%) of the diol. The enantiomeric excess of the diol was determined by HPLC analysis of the derived bis-acetate (Pirkle Covalent Phenyl Glycine column using 10% isopropanol/hexane mixture as eluant. Retention times are: t$_1$=25.9 minutes; t$_2$=26.7 minutes) to be 84%.

EXAMPLE 11

Asymmetric Dihydroxylation of trans-Stilbene in the presence of Boric Acid

To a well-stirred mixture of 58.2 mg (0.125 mmol; 0.25 eq) of the p-chlorobenzoate of hydroquinidine, 70 mg (0.6 mmol; 1.2 eq.) of N-methylmorpholine N-oxide, 37 mg (0.6 mmol; 1.2 eq.) of boric acid, 0.5 mL of dichloromethane, and OsO$_4$ (4.2 µL of a solution prepared using 121 mg OsO$_4$/mL toluene; 0.004 Mol %, 0.004 eq.) at room temperature, a dichloromethane solution (1 mL) of 90 mg (0.5 mmol) of trans-stilbene was added slowly, with a gas-tight syringe controlled by a syringe pump and with the tip of the syringe needle immersed in the reaction mixture, over a period of 24 h. After the addition was complete, 10% NaHSO$_3$ solution (2.5 mL) was added to the mixture, and the resulting mixture was stirred for 1 h. Organic materials were extracted with ethyl acetate, and the combined extracts were washed with brine and dried over Na$_2$SO$_4$. The solvent was evaporated under reduced pressure, and the residual oil was subjected to column chromatography on silica gel (5 g, elution with hexane-ethyl acetate, 2:1 v/v, R$_f$0.17) to afford 78.3 mg (73%) of the diol. The enantiomeric excess of the diol was determined by $^1$H-NMR (solvent: CDCl$_3$) analysis of the derived bis-Mosher ester to be 94%.

EXAMPLE 12

Asymmetric Dihydroxylation of trans-Methyl 4-methoxycinnamate in the presence of Boric Acid To a well-stirred mixture of 116.3 mg (0.25 mmol; 0.25 eq.) of the p-chlorobenzoate of hydroquinidine, 175.8 mg (1.5 mmol; 1.5 eq.) of N-methylmorpholine N-oxide, 74.4 mg (1.2 mmol; 1.2 eq.) of boric acid, 1 mL of dichloromethane, and OsO$_4$ (8.4 µL of a solution prepared using 121 mg OsO$_4$/mL toluene, 0.004 mol %, 0.004 eq.) at room temperature, a dichloromethane solution (1 mL) of 192 mg (1 mmol) of trans-methyl 4-methoxycinnamate was added slowly, with a gas-tight syringe controlled by a syringe pump and with the tip of the syringe needle immersed in the reaction mixture, over a period of 24 h. After the addition was complete, 10% NaHSO$_3$ solution (5 mL) was added to the mixture, and the resulting mixture was stirred for 1 h. Organic materials were extracted with ethyl acetate, and the combined extracts were washed with brine and dried over Na$_2$SO$_4$. The solvent was evaporated under reduced pressure, and the residual oil was subjected to column chromatography on silica gel (10 g, elution with hexane-ethyl acetate, 2:1 v/v, R$_f$ 0.09) to afford 151.1 mg (67%) of the diol. The enantiomeric excess of the diol was determined by HPLC analysis of the derived bis-acetate (Pirkle Covalent Phenyl Glycine column using 10% isopropanol/hexane mixture as eluant. Retention times are: t$_1$=24.0 minutes; t$_2$=24.7 minutes) to be 76%.

EXAMPLE 13

Asymmetric Dihydroxylation of trans-$\beta$-Methylstyrene in the presence of Boric Acid To a well-stirred mixture of 58.2 mg (0.125 mmol; 0.25 eq) of the p-chlorobenzoate of hydroquinidine, 70 mg (0.6 mmol; 1.2 eq) of N-methylmorpholine N-oxide, 72 mg (0.6 mmol; 1.2 eq) of phenylboric acid, 0.5 mL of dichloromethane, and OsO$_4$ (4.2 µL [of a solution prepared using 121 mg OsO$_4$/mL toluene; 0.004 Mol %, 0.004 eq) at 0° C., a dichloromethane solution] (0.5 mL), 65 µL (0.5 mmol) trans-$\beta$-methylstyrene was added slowly, with a gas-tight syringe controlled by a syringe pump and with the tip of the syringe needle immersed in the reaction mixture, over a period of 24 h. After the addition was complete, 10% NaHSO$_3$ solution (2.5 mL) was added to the mixture, and the resulting mixture was stirred for 1 h. Organic materials were extracted with ethyl acetate, and the combined extracts were washed with brine and dried over Na$_2$SO$_4$. The solvent was evaporated under reduced pressure, and the residual oil was subjected to column chromatography on silica gel (5 g, elution with hexane-ethyl acetate, 2:1 v/v, R$_f$0.62) to afford 109 mg (91%) of the phenylborate. The phenylborate was dissolved into acetone (3 mL) and 1,3-propandiol (0.5 mL), and the resulting mixture was stood for 2 h at room temperature. The solvent was evaported under reduced pressure, and the residual oil was subjected to column chromatography on silica gel (5 g, elution with hexaneethyl acetate, 2:1 v/v, R$_f$0.10)

to afford 48.6 mg (70%) of the diol. The enantiomeric excess of the diol was determined by HPLC analysis of the derived bis-acetate (Pirkle 1A column using 0.5% isopropanol/hexane mixture as eluant. Retention times are: $t_1 = 17.1$ minutes; $t_2 = 18.1$ minutes) to be 73%.

EXAMPLE 14

General Method for the Asymmetric Dihydroxylation of trans-Stilbene Using A Polymeric Alkaloid Ligand To a magnetically stirred suspension of the alkaloid copolymer (such as polymers 2–4, Table 1; 0.25 eq based on alkaloid incorporated), NMO (1.5 eq), and tetraethylammonium acetate tetrahydrate (1.0 eq) in acetone-water (10/1, v/v) a solution of $OsO_4$ (0.01 eq) in either toluene or acetonitrile was added. After stirring for 10–30 minutes, trans-stilbene (1.0 eq) was added and the reaction mixture was stirred for the given time and monitored by silica gel TLC (hexane-EtOAc 2/1, v/v). The concentration of olefin in the reaction mixture was 0.3–0.4M. After the reaction was complete, the mixture was diluted with acetone, water, hexane or ether and centrifuged or filtered to separate the polymer from the reaction mixture. The supernatant was then worked up as described by Jacobsen et al., *J. Am. Chem. Soc.*, 110:1968 (1988).

EXAMPLE 15

Asymmetric Dihydroxylation of trans-Stilbene Using A Polymer-Bound Alkaloid Ligand and Potassium Ferricyanide To a well-stirred mixture of the alkaloid polymer (0.05 mmol, based on alkaloid incorporated), potassium ferricyanide (0.198 g, 0.6 mmol) and potassium carbonate (0.83 g, 0.6 mmol) in tert-butanol (1.5 mL) and water (1.5 mL), was added $OsO_4$ solution (0.0025 mmol) in acetonitrile. After stirring for 10 min, trans-stilbene (36 mg, 0.2 mmol) was added and the mixture was stirred for the given time and monitored by silica gel TLC. When the reaction was complete, water (3.0 mL) was added and the mixture was filtered. The filtrate was extracted with dichloromethane (5 mL×2). the organic layer was stirred for 1 h with excess sodium metabisulfite and sodium sulfate. This suspension was filtered and the filtrate was concentrated to provide crude diol, which was purified on a silica gel column.

EXAMPLE 16

Asymmetric Dihydroxylation of Olefins in the Presence of Potassium Ferricyanide

The general procedure for asymmetric dihydroxylation of olefins using potassium ferricyanide:

To a well-stirred mixture of 0.465 g (1 mmol, 0.5 equiv=0.033M in ligand) dihydroquinidine p-cholorobenzoate (Aldrich, 98%), 1.980 g (6 mmol, 3.0 equiv) potassium ferricyanide, 0.830 g (6 mmol, 3.0 equiv) potassium carbonate, and 0.5 mL of a 0.05M tert-butyl alcohol solution of osmium tetroxide (0.025 mmol, 0.0125 equiv) in 30 mL of a tert-butyl alcohol-water mixture (1:1, v/v) at room temperature, olefin (2 mmol) was added at at once. The reaction mixture was stirred for 24 h at room temperature. Solid sodium sulfite ($Na_2SO_3$, 1.5 g) was added, and the mixture was stirred for an additional hour. The solution obtained was concentrated to dryness under reduced pressure, and the residue was extracted with three portions of ether. The combined extracts were dried ($Na_2SO_4$) and evaporated. The residue was purified by column chromatography (silica gel, dichloromethane-ether).

EXAMPLE 17

Preparation of 9-O-Phenyldihydroquinidine

To a suspension of dihydroquinidine (4.0 g) in THF (40 mL) was added η-BuLi (2.5M solution in hexane, 4.95 mL) at 0° C. The ice bath was removed and the reaction mixture stood at room temperature for 10 minutes. To the resulting yellow solution, solid cuprous chloride (1.2 g) was added. After stirring for 30 minutes, pyridine (30 mL) and HMPA (1 mL) were added. After stirring for 5 minutes, phenyl iodide (1.37 mL) was added and the mixture was stirred at reflux for 36 h. To the resulting mixture, $aqNH_4OH$ was added and the mixture was extracted with ethyl ether. The extract was dried over $MgSO_4$. The solvent was evaporated under reduced pressure, and the residue was subjected to column chromatography on silica gel (100 g, elution with ethyl acetate-ethanol, 9:1 v/v, Rf 0.23) to afford 1.77 g(y. 36%) of 9-O-phenyldihydroquinidine.

$^1H$ NMR ($CDCl_3$)δ8/68 (1H, d, J=4.5 Hz), 8.08 (1H, d, J =9 Hz), 7.3–7.5 (3H, m), 7.17 (2H, t, J=8 Hz), 6.89 (1H, t, J=8 Hz), 6.78 (2H, d, J=8 Hz), 6.02 (1H, d, J =3 Hz), 4.00 (3H, s), 2.7–3.3 (5H, m), 2.2–2.4 (1H, m), 1.4–1.9 (6H, m), 1.1–1.3 (1H, m), 0.97 (3H, t, J=7 Hz).

EXAMPLE 18

Asymmetric Dihydroxylation of Trans-3-Hexene Using 9-O-Phenyldihydroquinidine and Potassium Ferricyanide To a well-stirred mixture of 46 mg of 9-O-phenyldihydroquinidine, 396 mg of potassium ferricyanide, 166 mg of potassium cabonate and 8 μL of a 0.63M toluene solution of osmium tetroxide in 6 mL of t-butyl alcohol-water (1:1, v/v) at room temperature was added 50 μL of trans-3-hexene all at once. The reaction mixture was stirred for 20 h at room temperature. Solid sodium sulfite was added and the mixture was stirred for 3 h. The solid was removed by filtration and the filtrate was extracted with ethyl ether. The extract was dried over $mgSO_4$. The solvent was evaporated under reduced pressure, and the residue was subjected to column chromatography on silica gel (elution with hexane-ethyl acetate, 2:1 v/v) to afford 40.5 mg (y. 85%) of the diol. The enantiomeric excess of the diol was determined by GLC analysis of the derived bis-Mosher ester to be 83% (5% phenyl-methylsilicone, 0.25 m film, 0.317 mm diameter, 29 m long. Retention times are $t_1 = 15.6$ min; $t_2 = 16.0$ min.).

EXAMPLE 19

Asymmetric Oxyamination of Trans-Stilbene Using N-Chloro-N-Sodio-t-Butylcarbamate To a well-stirred mixture of 81 mg trans-stilbene, 122 mg of N-chloro-N-sodio-t-butylcarbamate, 95 mg of murcuric chloride, 209 mg of dihydroquinidine p-chlorobenzoate and 370 μL of water acetonitrile (5 mL) was added 9 μL of a 0.5M toluene solution of osmium tetroxide. The mixture was stirred at room temperature overnight. Solid sodium sulfite and water were added, and the mixture was stirred at 60° C. for 1 hour. The mixture was extracted with dichloromethane and the extract was dried over $MgSO_4$. The solvent was evaporated under reduced pressure, and the residue was subjected to column chromatography on silica gel (elution with hexane-ethyl acetate, 4:1 v/v, Rf 0.13) to afford 131 mg (y. 93%) of the aminoalcohol. The enantiomeric excess of the aminoalcohol was determined by HPLC analysis (Pirkle Covalent Phenyl Glycine column using 10% isopropanol/hexane mixture as eluant. Retention times are: $t_1 = 2.7$ min; $t_2 = 15.2$ min.) to be 65%. $^1$H NMR (CDCl$_3$)δ7.1-7.4 (10H, m), 5.3-5.4 (1H, m), 4.95 (1H, d, J=3.5 Hz), 4.8-5.0 (1H, m), 2.6-2.7 (1H, m), 1.34 (9H,).

EXAMPLE 20

Asymmetric Dihydroxylation Using Heterocyclic Chiral Ligands

Ligand preparations and properties

1a: To a room temperature suspension of DHQD (48.9 g, 0.15 mol) in dry DMSO (600 ml) are added NaH (4.0 g, 0.17 mmol) followed by pyridine (12.1 ml, 0.15 mol), CuI (28.6 g, 0.15 mol), and then 9-phenanthryl iodide (45.6 g, 0.15 mol) under argon. After 70 h of reaction at 120° C., 1a is obtained in 73% yield (55.0 g). See also: Lindley, J. Tetrahedron, 1984, 40, 1433 and references therein.

m.p. 98°-100° C., $^1$H NMR (250 MHz, CDCl$_3$) δ=8.7 (m,2), 8.38 (d,1), 8.07 (d,1), 7.75 (m,2), 7.57 (d,1), 7.4 (m,6), 6.63 (s,1), 6.63 (d,1), 4.03 (s,3), 3.38 (m,1), 3.16 (m,1), 2.97 (m,2), 2.78 (m,1), 2.55 (s,br.,1), 2.39 (t,1), 1.81 (s,1), 1.6 (m,6), 0.98 (t,3), $^{13}$C NMR (75 MHz, CDCl$_3$)δ=158.2, 150.4, 147.5, 144.6, 143.7, 132.3, 132.0, 131.5, 127.4, 127.2, 126.7, 126.6, 126.4, 124.5, 122.8, 122.2, 121.9, 118.1, 104.8, 100.9, 78.8, 60.3, 55.8, 51.0, 50.1, 37.4, 27.1, 26.6, 25.2, 21.7, 11.8. IR (KBr): ν=1622, 1508, 1452 and 1227 cm$^{-1}$. [α]D$^{23}$= −281.3 (CHCl$_3$, c=1.12 g ml$^{-1}$).

1b: To a room temperature suspension of DHQD (65.2 g, 0.20 mol) in DMF (300 ml) are added NaH (6.06 g, 0.24 mol), followed by 2-chloro-4-methylquinoline (42.6 g, 0.24 mol). After stirring for 24 h at room temperature, 2a is obtained in 82% yield (76.3 g).

m.p. 151°-153° C. $^1$H NMR (250 MHz, CDCl$_3$) δ=0.93 (3H,t,J =7.2Hz), 1.4-1.7 (6H,m), 1.76 (1H,s), 2.12 (1H,t,J=10.0Hz), 2.61 (3H,s), 2.7-3.0 (4H,m), 3.43 (1H,dd,J=6.4,8.8Hz), 3.94 (3H,s), 6.82 (1H,s), 7.2-7.6 (6H,m), 7.73 (1H,d,J=2.5Hz), 7.81 (1H,d,J=8.0Hz), 7.98(1H,d,J =9.2Hz), 8.67 (1H,d,J=4.6Hz). $^{13}$C NMR (CDCl$_3$)δ=11.8, 18.4, 22.9, 25.2, 25.8, 27.1, 37.2, 49.8, 50.6, 55.4, 59.2, 73.1, 101.7, 112.5, 118.5, 121.4, 123.3, 123.7, 125.2, 127.5, 129.0, 131.3, 144.5, 145.8, 147.3, 157.4, 160.4.IR(KBr): 1608, 1573, 1508, 1466, 1228, 1182, 1039, 848, 758 cm$^{-1}$. [α]D$^{21}$= −194.7° (EtOH, c=1.0). 2a and 2b can be synthesized in a similar fashion. Like the p-chlorobenzoate derivatives, these two new types of ligands are now available from Aldrich.

Typical Procedure for the Catalytic ADH (vinlycylooctane)

To a well-stirred mixture of DHQD-PHN 1a (100 mg, 0.2 mmol. 0.02 equiv.), K$_3$Fe(CN)$_6$(9.88 g, 30 mmol, 3 equiv.), and K$_2$CO$_3$ (4.15 g, 30 mmol, 3 equiv.) in a tert-BuOH-H$_2$O mixture (100 ml, 1/1, v/v) was added potassium osmate (VI) dihydrate (7.4 mg, 0.02 mmol, 0.002 equiv.). The resulting yellow solution was cooled to 0° C. and vinylcyclooctane (1.65 ml, 10 mmol) was added. The reaction mixture was stirred for 18 h at 0° C. Na$_2$SO$_3$ (7.5 g) was added and the resulting mixture was stirred for 30 minutes. The two phases were separated and the aqueous phase was then extracted with CH$_2$Cl$_2$. The combined organic solution was evaporated and the residue was diluted with ethyl acetate, washed with 1M H$_2$SO$_4$, aqueous NaHCO$_3$, and brine, and dried. Concentration and flash chromatography affored 1.63 g (95%) of cyclooctylethanediol as a colorless oil; [α]D$^{22}$= −4.1° (EtOH, c=1.0). The ee of the diol was determined by HPLC analysis of the derived bis-MTPA ester to be 93%. The alkaloid ligand was recovered in 82% yield by adjusting the acidic aqueous washes to pH 11 with Na$_2$CO$_3$, extracting with CH$_2$Cl$_2$.

EXAMPLE 21

Asmmetric Dihydroxylation of Olefins Using 9-O-phenanthryl and 9-O-naphthyl dihydroquinidine Ligands This example describes the enantioselectivity-ligand structure relationship of the 9-O-aryl DHQD ligands which explains the advantages of these new ligands.

The enantiometric excesses obtained in the catalytic ADH reactions of various olefins using 9-O-aryl DHQD are summarized in Table 13. These 9-O-aryl DHQD ligands can be easily prepared in one step from commercially available hydroquinidine, NaH, CuI, and the corresponding aryl halide in moderate to good yields (52-70%), as describe below. Compared to DHQD p-chlorobenzoate 1,

TABLE 13

Catalytic Asymmetric Dihydroxylation of Olefins[a]

ee[b], c[f]

| olefin: | Ph-CH=CH-Ph | Ph-CH=CH-Me | Ph-CH=CH-CO₂Me | Bu-CH=CH-Bu | Et-CH=CH-Et | C₅H₁₁-CH=CH-CO₂Et |
|---|---|---|---|---|---|---|
| 1 (4-ClC₆H₄C(O)–) | 99 | 91 | 91 | 79 | 74 | 67 |
| 2 (Ph–) | 94 | 89 | 91 | 88 | 83 | 88 |
| 3 (1-naphthyl–) | 99 | 91 | 96 | 94 | 92 | 94 |

R group on DHQ catalyst (MeO-quinoline with OR, OH substituents):
1: 4-chlorobenzoyl
2: phenyl
3: 1-naphthyl

TABLE 13-continued

Catalytic Asymmetric Dihydroxylation of Olefins[a]

ee[b], %

| olefin: | | | | | | |
|---|---|---|---|---|---|---|
| | 99 | 93 | 98 | 96 | 92 | 94 |

[a] All reactions were carried out as described by Kwong, H.-L., et al., Tetrahedron Lett., 30,2041 (1989), except that 25 mol % of ligand was used. Reactions were performed at room temperature. In all cases the isolated yield of the diol was 75-95%.
[b] The enantiomeric excesses were measured by conversion of the diol into the corresponding biesters of (R)-(+)-α-methoxytrifluoromethylphenylacetic acid and determination of the ratio of diastereomers by GLC, HPLC, and/or $^1$H 9-O-phenyl DHQD 2 is obviously a better ligand for aliphatic olefins, but not for aromatic olefins. By contrast, 9-O-naphthyl 3 and especially, 9-O-phenanthryl DHQD 4 exhibit much higher enantioselectivities for both aromatic and aliphatic olefins.

In order to obtain information regarding the relationship between ligand structure and enantioselectivity in the ADH, various 9-O-substituted DHQD derivatives were next examined. The structures of the 9-O-substituents of these DHQD derivatives and their enantioselectivities for the typical aliphatic and aromatic olefins, trans-5-decene and trans-stilbene are shown in Table 14. Each structure in Table 14 is drawn with its expected spatial orientation in the reaction intermediate, osmate ester such that the more sterically hindering 6-methoxyquinoline moiety is on the left side of the structure[11].

In Group A, those derivatives having a second benzene ring on the right side (1,3 and 4) all give higher ee's for stilbene (99%) than the one (2) without that second benzene ring (94%). In addition, the naphthyl derivative (3) gives higher ee for decene (94%) than does the phenyl derivative (2) (88%). These two results suggest that the benzene ring on the right side is important for high enantioselectivities with both aliphatic and aromatic olefins. On the other hand, the fact that derivatives (2-4) give much higher ee's for decene (88-96%) than does the p-chlorobenzoate derivative (1) (79%) shows the importance of the aromatic ring on the left side for aliphatic olefins.

Next, the o-position of the phenyl derivatives was examined (2, 5-7, Group B). While the phenyl-derivative (2) and the 2-methylphenyl derivative (6) give fairly high ee's for decene (88, 91%), the 2-pyridyl (5) and the 2,6-dimethylphenyl (7) derivatives do not produce satisfactory enantioselectivities (71, 50%). This indicates that the left o-position of the phenyl derivative needs to be just C—H for high enantioselectivity. The effect at m- and p-positions can be understood by comparing the derivatives in Group C and D. These results indicate that both the m- and p-positions need to be C—H or larger for high ee's with aliphatic olefins.

TABLE 14

TABLE 14-continued

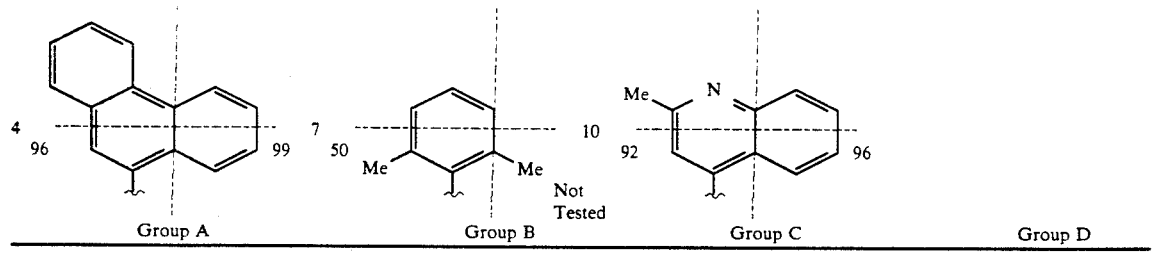

| | Group A | | Group B | | Group C | | Group D |
|---|---|---|---|---|---|---|---|
| 4 | 96 | 99 | 7 | 50 | 10 | 92 | 96 |
| | | | | | Not Tested | | |

Procedure for the Synthesis of 9-O-aryl DHQD (3) and (4)

Into a 100 ml 3-necked round-bottomed flask 2.00 g (6.12 mmol) of dihydroquinidine (Note: All addition of reagents and reaction were done under argon) and 0.160 g (6.73 mmol) of NaH were dissolved in 20 ml of dimethylsulfoxide. After stirring for about 10 minutes the reaction mixture became a clear orange-yellow solution. At this point, 1.17 g (6.12 mmol) of copper(I) iodide and 0.50 ml (6.12 mmol) of pyridine and 6.12 mmol of 1-naphthyl iodide or phenanthryl bromide, respectively, were added and the reaction mixture was heated for 3 days at 120° C. Then the reaction mixture was allowed to cool down to room temperature and dichloromethane (30 ml) and water (30 ml) were added. Next, 10 ml of concentrated ammonium hydroxide was slowly added to the reaction mixture. After stirring for 15 minutes the two phases were separated. The aqueous phase was extracted two times with dichloromethane (20 ml). The organic phases were combined, washed three times with water (10 ml), and evaporated. The resulting residue was then purified by column chromatography (silica gel, using 5% methanol/ethyl acetate as the eluting solvent), yielding slightly yellow crystals of 9-O-naphthyl DHQD (3) (yield: 70%) or 9-O-phenanthryl DHQD (4) (yield: 52%) respectively.

(3) m.p. 75°-77° C. $^1$H NMR (250 MHz, CDCl$_3$): $\delta = 8.60$ (dd,2), 8.05 (dd,1), 7.80 (d,1), 7.4 (m,5), 7.07 (t,1), 6.42 (d,1), 6.24 (d,1), 3.99 (s,3), 3.31 (dt,1), 3.17 (dd,1), 2.92 (dd,2), 2.78 (m,1), 2.37 (m,2), 1.79 (s,br., 1), 1.6 (m,6), 0.96 (t,3). $^{13}$C NMR (75 MHz, CDCl$_3$): $\delta = 158.2$, 150.4, 147.5, 132.3, 132.0, 131.5, 127.4, 127.2, 126.7, 126.6, 126.4, 124.5, 122.8, 122.2, 121.9, 118.1, 104.8, 100.9, 78.8, 60.3, 55.8, 51.0, 50.1, 37.4, 27.1, 26.6, 25.2, 21.7, 11.8, IR (KBr): $\nu = 1622$, 1508, 1452 and 1227 cm$^{-1}$. $[\alpha]_D^{23} = -281.3$ (CHCl$_3$, c = 1.12 g ml$^{-1}$)

The 9-O-aryl DHQD (3) and (4) were prepared according to the Ullmann phenyl ether synthesis: Lindley, J., *Tetrahedron*, 40:1433 (1984) and references therein.

All these 9-O-substituted DHQD derivatives (5), (9) and (10) were synthesized at room temperature without copper(I) iodide.

EXAMPLE 22

Asymmetric Dihydroxylation of Olefins Using Dihydroquinine Arylethers

A high level of asymmetric induction was achieved in the asymmetric dihydroxylation of a wide variety of olefins using 9-O-aryldihydroquinines as ligands. (B. Lohray, et al., *Tetrahedron Lett.*, 30:2041 (1989))

The asymmetric dihydroxylation using catalytic amounts of osmium tetroxide and cinchona alkaloid derivatives is one of the few examples of reactions combining high levels of enantioselectivity for a large range of substrates, good to excellent yields, simple and mild experimental conditions. Another point worth emphasizing, is the availability of the requisite cinchona alkaloids. Both enantiometers of the diol can be obtained choosing dihydroquinine (DHQ) or dihydroquinidine (DHQD) derivatives:

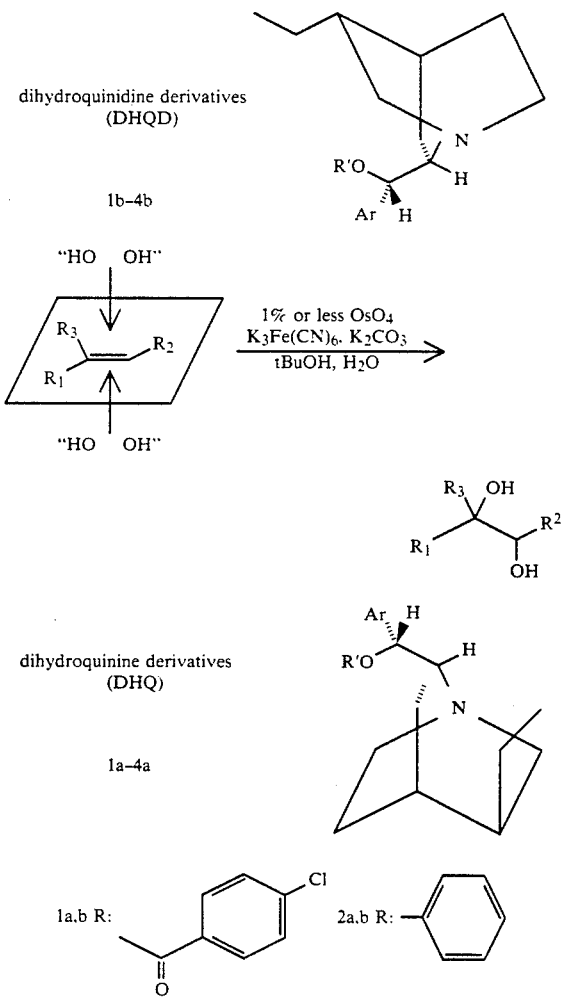

-continued

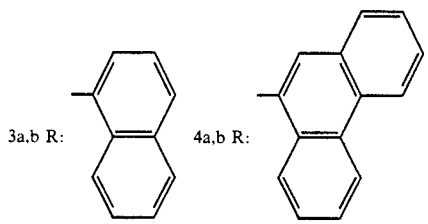

3a,b R: (naphthyl)   4a,b R: (phenanthryl)

Recent advances in our group using potassium ferricyanide as stoichiometric oxidant and new aryl and heteroaromatic derivatives of the dihydroquinindine and dihydroquininine have made it possible to obtain good to excellent yields and enantioselectivities for many different kinds of substrates. (H-L. Kwong, et al., *Tetrahedron Lett.*, 31:2999; M. Minato, et al., *J. Org. Chem.*, 55:766 (1990); T. Shibata, et al., *Tetrahedron Lett.*, 31:3817 (1990); In this example we report details about the 9-O-aryldihydroquinines 2a–4a.

The trend for the dihydroquinine and dihydroquinidine derivatives are very similar (see Table 15). As in the dihydroquinidine series, the DHQ phenanthryl ether derivative 4a is greatly superior to 1a for a wide range of substrates. The improvement is especially dramatic for transdisubstituted aliphatic olefins such as 5-decene (entry 1) as well as for terminal saturated olefins (entries 6 and 7) and for alkyl substituted $\alpha,\beta$ unsaturated carbonyl compounds (entry 3). The changes observed in case of aromatic olefins (entries 4 and 5) were slight.

Unlike the difference observed using the dihydroquinidine derivatives, the gap in enantioselectivities between naphthyl-DHQ and phenanthryl-DHQ is significant ($\Delta$ee=2-10% at RT versus 1-4% for DHQD derivatives). Especially noteworthy is the fact that the differences of selectivities obtained using 4a and 4b is very small for all examples in Table 12 and therefore enantiomers of the diol are available in almost the same optical purity.

The reaction can be successfully carried out at 0° C. with a significant improvement of enantioselectivity especially for terminal olefins (entries 1,3 and 7).

In conclusion, we want to point out that from a large variety of olefinic substrates, it is now possible to obtain vicinal diols in excellent yields, with good to excellent enantiomeric enrichments for both diol enantiomers using either dihydroquinine or dihydroquinidine.

EXAMPLE 23

Synthesis of Methylphenylcarbamoyl dihydroquinidine (MPC-DHQD)

Dihydroquinidine (1.4 g, 4.3 mmol, 1 eq) was dissolved in 15 ml of $CH_2Cl_2$ under nitrogen atmosphere in a 3-necked 100 ml round bottom flask. At room temperature, 2 ml of triethylamine (14.4 mmol, 3.3 eq) was added to the solution and stirred for 30 minutes. N-methyl-N-phenylcarbamoyl chloride (1.6 g, 9.4 mmol, 2.2 eq) was dissolved in 6 ml $CH_2Cl_2$ and added to the reaction mixture dropwise via an addition funnel. The reaction mixture was stirred under $N_2$ for three days before reaching reaction completion. 50 ml of 2N NaOH were added, and the phases were separated. The CH$_2$Cl$_2$ layer was saved and the aqueous phase was extracted with 50 ml of $CH_2Cl_2$. The $CH_2Cl_2$ phases were combined and dried over $MgSO_4$ before being concentrated down to afford a gummy pink material.

TABLE 15

$$R_1\text{-CH=CH-}R_2 \xrightarrow[\text{t-butanol/H}_2\text{O}]{\substack{1\text{ mol \% OsO}_4 \\ 25\text{ mol \% 1-4 a or b} \\ K_3Fe(CN)_6/K_2CO_3}} R_1\text{-CH(OH)-CH(OH)-}R_2$$

| entry | olefin | ee using 1a (ee using 1b) | ee using 2a (ee using 2b) | ee using 3a (ee using 3b) | ee using 4a (ee using 4b) |
|---|---|---|---|---|---|
| 1 | nBu-CH=CH-nBu | 70% (79%) | 75% (88%) | 86% (94%) | 91% (96%) [93%]$^{0°C.}$ |
| 2 | (2-hexene) | 67% (74%) | 75% (83%) | 82% (92%) | 85% (94%) |
| 3 | (α,β-unsaturated ethyl ester) | 64% | 70% | 83% | 91% [94%]$^{0°C.}$ |
| 4 | Ph-CH=CH-Ph | 97% (99%) | 93% (94%) | 94% (99%) | 96% (99%) |
| 5 | styrene | 66% (74%) | 57% (61%) | 62% (72%) | 69% (73%) |
| 6 | 1-decene | 41% (45%) | 44% | 56% (66%) | 63% |
| 7 | (vinylcyclooctane) | 54% (64%) | 58% | 73% (84%) | 83% (88%) [88% (93%)]$^{0°C.}$ |

All but the three indicated reactions were carried out at room temperature. In all cases the isolated yield was 70-95%. Enantiomeric excesses were determined by GC or HPLC analysis of the derived bis-Mosher esters.

Purification via flash chromatography (silica gel, 95.5 EtOAc/Et₃N, v/v) afforded a yellow material which was then crystallized from CH₃CN to obtain white starlike crystals (1.27 g, 65% yield).

Characterization mp. 119°–120° C. High resolution mas spec; calculated molecular mass-459.25217 amu, found-459.2519 amu. ¹H NMR (300 MHz, CDCl₃ with TMS); 8.7 $\delta$ (d, 1H), 8.0 $\delta$ (d,1H), 7.2–7.4 $\delta$ (m, 7H) 6.4 $\delta$ (d, 1H), 3.8 $\delta$ (s,3H), 3.3 $\delta$ (s,3H), 3.1 $\delta$ (1H), 2.8 $\delta$ (q, 1H), 2.6 $\delta$ (m, 3H), 1.7 $\delta$ (s,2H), 1.3–1.4 $\delta$ (m7H), 0.9 $\delta$ (t, 3H). ¹³C NMR (75 MHz, CDCl₃ with TMS): 12.1 $\delta$, 23.9 $\delta$, 25.3 $\delta$, 26.2 $\delta$, 27.3 $\delta$, 37.5 $\delta$, 38.2 $\delta$, 49.8 $\delta$, 50.7 $\delta$, 55.5 $\delta$, 59.7 $\delta$, 75.6 $\delta$, 75.6 $\delta$, 101.8 $\delta$, 119.1 $\delta$, 121.8 $\delta$, 126.3 $\delta$, 126.7 $\delta$, 127.3 $\delta$, 129.1 $\delta$, 131.7 $\delta$, 143.1 $\delta$, 144.7 $\delta$, 144.9 $\delta$, 147.5 $\delta$, 152.1 $\delta$, 154.8 $\delta$, 157.7 $\delta$.

EXAMPLE 24

Asymmetric dihydroxylation of Olefins Using 9-O-Carbamoyl Dihydroquinidine Ligands Typical Procedure for the Catalytic ADH (cis-$\beta$-methylstyrene)

To a well-stirred solution of DHQD-MPC (dihydroquinidine methylphenylcarbamate) (10 mg, 0.02 mmol, 0.10 equiv), K₃Fe(CN)₆ (200 mg, 0.6 mmol, 3 equiv), K₂CO₃ (85 mg, 0.6 mmol, 3 equiv) in a tert-butanol/water solution (6 ml, 1/1, v/v), osmium tetroxide was added in acetonitrile solution (0.5M, 4 μl, 0.01 equiv) at room temperature. After stirring for ten minutes, cis-$\beta$-methylstyrene (26 μl, 0.2 mmol) was added. The reaction mixture was stirred at room temperature, and reaction progress was monitered by thin layer chromatography. Upon reaction completion (less than two hours), the phases were separated. The aqueous phase was extracted with CH₂Cl₂. The tert-butanol and CH₂Cl₂ fractions were combined and stirred for one hour with excess sodium metabisulfite and sodium sulfate. Concentration followed by flash chromatography afforded the diol (24.4 mg, 82% yield) as an off-white solid. Enantiomeric excess (ee) of the diol (46% ee) was determined by GC analysis of the bis-MPTA ester derivative.

EXAMPLE 25

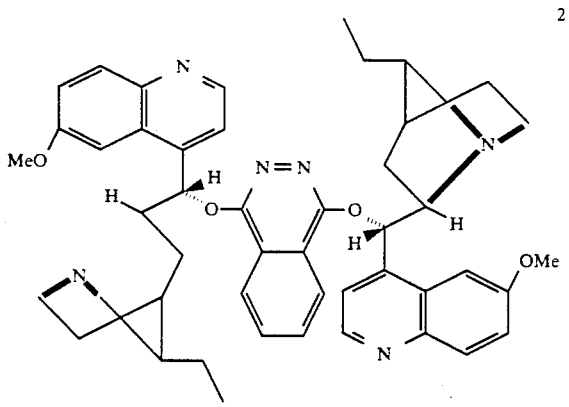

Synthesis of
1,4-bis-(9′-O-dihydroquinidyl-phthalzaine(2)

A 50 mL three-necked round-bottomed flask equipped with an efficient magnetic stir bar and inert gas in- and outlet was charged with dihydroquinidine (2.00 g, 6.12 mmol) (ground in a mortar). The flask was flushed for 30 min with a gentle stream of argon. Anhydrous dimethyl formamide (20 mL, Fisher Chemicals, 0.03% water contents) was added and the reaction mixture stirred at room temperature until a clear solution formed. Sodium hydride (0.16 g, 6.67 mmol) was added and the reaction mixture stirred for 60 min to yield an orange, slightly cloudy solution of the sodium alcoholate of dihydroquinidine which was reacted with 0.55 g (2.78 mmol) 1,4-dichlorophthalazine for 24 h at room temp. and for 24 h at 115° C. (oil bath temp.). The brown solution was transferred into a separatory funnel diluted with 50 mL methylene chloride and washed with 50 mL water. The aqueous phase was separated and extracted three times with methylene chloride. The combined organic layers were washed with water (100 mL) and with brine (100 mL), dried (MgSO₄) and concentrated in vacuo. The remaining brown oil was purified by column chromatography (silica gel 60, methanol/ethyl acetate, 1/1, v/v; $R_f$=0.25) to yield 1.02 g (43%) 1,4-bis-(9-O-dihydroquinidyl)-phthalazine (2) as a colorless powder.

Physical Data: C₄₈H₅₄N₆O₄ (779.0), ¹H NMR (300 MHz): $\delta$=8.67(d, J=4.5Hz, 2H), 8.36-8.34(m, 2H), 8.01(d, J=9.2Hz, 2H), 7.96-7.94(m, 2H), 7.59(d, J=2.7Hz, 2H), 7.47(d, J=4.6Hz, 2H), 7.38(dd, J=9.2, 12.7Hz, 2H), 7.00(d, J=6.7Hz, 2H), 3.93(s, 6H), 3.45(q, J=5.1Hz, 2H), 2.82-2.64(m,8H), 2.04-1.92(m,2H), 1.72(s,br. 2H), 1.61-1.40(m, 10H), 0.83(t, J=6.9Hz); $[\alpha]_D^{19}$= –197.9 (c 1.0, CHCl₃); m.p.=81°-84° C.

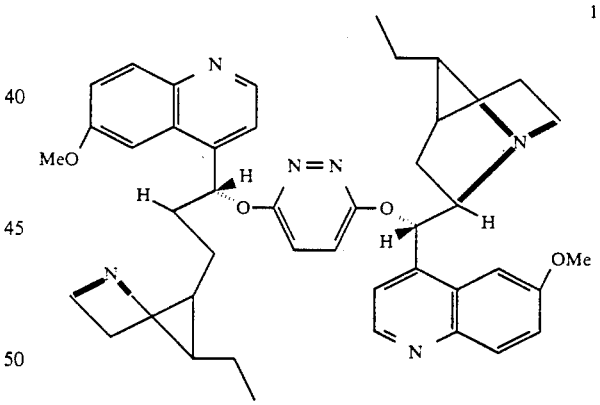

(B) Synthesis of
3,6-Bis-(9′-O-dihydroquinidyl)-pyridazine (1)

A synthesis procedure similar to that described in part (A) was performed using 3,6-dichloropyridazine rather than 1,4-dichlorophthalazine.

Physical data: C₄₄H₅₂N₆O₄ (728.9); yield: 34%; ¹H NMR (300 MHz): $\delta$=8.65(d, J=7.5Hz, 2H), 7.98(d, J=9.2HZ, 2H), 7.44(d, J=2.7Hz, 2H), 7.37-7.33(m, 2H), 7.00(s, 2H), 6.74(d J=6.1Hz, 2H), 3.87(s, 6H), 3.24(q, J=7.3Hz, 2H), 2.82-2.55(m, 8H), 1.93(1.85(m, 2H), 1.68(s, br., 2H), 1.59-1.30(m 10H), 0.83(t, J=6.8Hz, 6H); $[\alpha]_D^{19}$= +5.9 (c 1.1, CHCl₃); m.p. =109°-110° C.

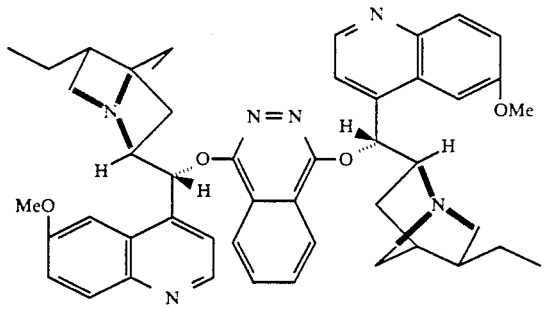

3

(C) Synthesis of 1,4-Bis-(9'-O-dihydroquinyl)-phthalazine (3)

A synthesis procedure similar to that described in part (A) was performed using dihydroquinine rather than dihydroquinidine.

Physical data: $C_{48}H_{54}N_6O_4$ (779.0); yield: 49%; $^1H$ NMR (300 MHz): $\delta$ = 8.65(d, J = 4.6Hz, 2H), 8.34–8.31(m, 2H), 7.98(d, J = 9.2Hz, 2H), 7.95–7.92(m, 2H), 7.58(d, J = 2.7Hz, 2H), 7.42(d, J = 2.7Hz, 2H), 7.35(dd, J = 2.7, 9.2HZ, 2H), 7.00(d, J = 5.8Hz, 2H), 3.91 (s, 6H), 3.47–3.41(m, 2H), 3.18–2.94(m, 4H), 2.61–2.49(m, 2H), 2.38–2.29(m 2H), 1.80–1.65(m, 8H), 1.49–1.22(m, 8H), 0.83(t, J = 7.1Hz, 6H); m.p. = 114°–116° C.

EXAMPLE 26

A typical procedure for catalytic asymmetric dihydroxylation using the chiral auxiliary To a well-stirred solution of bis-1,4-(9'-O-dihydroquinidine)phthalazine (7.8 mg, 0.01 mmol), potassium ferricyanide (0.99 g, 3 mmol), potassium carbonate (0.42 g, 3 mmol), and osmium tetroxide (0.1 mL of a 0.1M toluene solution, 0.01 mmol) in 15 mL of a tert-butyl alcohol-water (1:1, v/v) at 0° C., 1-decene (0.14 g, 0.19 mL, 1 mmol) was added in one portion. The mixture was stirred for 24 h at 0° C. Solid sodium sulfite (1.5 g) was added and the mixture was stirred for an additional hour, and then warmed up to room temperature. Ethyl acetate (10 mL) was added to the reaction mixture, and aqueous layer was extracted with ethyl acetate (3×5 mL). Combined organic layer was dried over anhydrous magnesium sulfate, and concentrated in vacuo. Crude product was purified by flash chromatography (silica gel, hexanes/EtOAc) to afford decane 1,2-diol as a white solid (0.145 g, 83%). HPLC analysis of the bis-Mosher ester of this crude decane 1,2 diol gave 84% ee.

TABLE 16

| ADH using 3,6-bis-(9'O-dihydroquinidyl)-pyridazine (1) as chiral auxiliary: | | |
|---|---|---|
| | ee values | |
| Substrate | DHQ—MEQ[a] | New Ligand 1 |
| styrene | 87% (0° C.) | 93% |

[a]K. Barry Sharpless, Willi Amberg, Matthias Beller, Hou Chen, Jens Hartung, Yasuhiro Kawanami, Doris Lübben, Eric Manoury, Yasukazu Ogino, Tomoyuki Shibata und Tatzuso Ukita, J. Org. Chem. 56(1991)4585:

| ADH using 1,4-bis-(9'-O-dihydroquinidyl)-phthalazine (2) as chiral auxiliary: | | |
|---|---|---|
| | ee values | |
| Substrates | DHQD—Phn or DHQ—MEQ[a] | New Ligand 2 |
| 1-decene | .74% (0° C.) | 79%<br>85% (0° C.) |
| styrene | 87% (0° C.) | 95% |
| 2-vinylnaphthalene | 93% (0° C.) | 98% |

| ADH using 1,4-bis-(9'-O-dihydroquinidyl)-phthalazine (2) as chiral auxiliary: | | |
|---|---|---|
| α-methylstyrene | 81% (0° C.) | 92%<br>94% (0° C.) |
| trans-5-decene | 95% | 96% |

TABLE 16-continued

| Substrate | | |
|---|---|---|
| 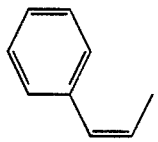 | 46% | 29% |

[a] K. Barry Sharpless, Willi Amberg, Matthias Beller, Hou Chen, Jens Hartung, Yasuhiro Kawanami, Doris Lübben, Eric Manoury, Yasukazu Ogino, Tomoyuki Shibata und Tatzuso Ukita. J. Org. Chem. 56(1991)4585.

| | ee values | |
|---|---|---|
| Substrates | phenanthryl-ODHQD | phthalazine-bis-ODHQD |
| styrene (PhCH=CH-) | 53% | 73% |
| α-methylstyryl | 48% | 79% |
| cyclo-C$_6$H$_{11}$-C≡C-CH=CH$_2$ | 45% | 72% |

ADH using 1,4-bis-(9'-O-dihydroquinyl)-phthalazine (3) as chiral auxiliary:

| | ee values | |
|---|---|---|
| Substrates | DHQ—MEQ[a] | New Ligand 3 |
| styrene | 77% | 94% |
| 2-vinylnaphthalene | — | 98% |
| α-methylstyrene | — | 90% |

[a] K. Barry Sharpless and Eric Manoury, unpublished result:[1]

ADH using 1,4-bis-(9'-O-quinyl)-phthalazine as chiral auxiliary:

| Substrate | ee value |
|---|---|
| 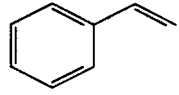 | New Ligand |
| | — 96% |

TABLE 17

Results of ADH Reactions (Using Various Amounts of Chiral Auxiliary:

$$C_8H_{17}-\!\!\!-\!\!\!/\!\!\!\!\!\diagdown \quad \xrightarrow[\substack{K_3Fe(CN)_6 \ 0.99 \ g \ (3 \ mmol) \\ K_2CO_3 \ 0.41 \ g \ (3 \ mmol) \\ \text{t-BuOH/H}_2O \ 15 \ mL(v/v \ 1:1) \\ 0° \ C., \ 24 \ h \\ OsO_4 \ 0.01 \ mmol \ (1 \ mol \ \%) \\ \text{Ligand}}]{} C_8H_{17}\!\!-\!\!\overset{OH}{\underset{\downarrow}{\!\!\!\diagdown}}\!\!-\!\!OH$$

0.14 g (1 mmol)

Ligand:

DHQD—O—C(=N—N=C)—O—DHQD (phthalazine bridge)

| Entry | Ligand (mmol) | Isolated Yield (%) | Ee (%) |
|---|---|---|---|
| 1 | 0.01 | 82 | 84.3 |
| 2 | 0.02 | 80 | 84.5 |
| 3 | 0.03 | 83 | 84.4 |
| 4 | 0.04 | 80 | 84.3 |

Equivalents

Those skilled in the art will recognize, or be able to ascertain, using no more than routine experimentation, many equivalents to the specific embodiments of the invention described specifically herein. Such equivalents are intended to be encompassed in the scope of the following claims.

We claim:

1. An osmium-catalyzed method of producing an asymmetrically dihydroxylated olefin, comprising combining olefin, a chiral auxiliary, an organic solvent, an aqueous solution, a base, an osmium-containing catalyst and a ferricyanide salt and maintaining the resulting combination under conditions appropriate for asymmetric dihydroxylation of the olefin to occur, wherein the chiral auxiliary is a cinchona alkaloid covalently linked to an organic substituent of at least 300 daltons molecular weight through a planar aromatic hydrocarbon or nitrogen containing heterocyclic spacer group.

2. The method of claim 1 wherein the organic substituent is an alkaloid.

3. The method of claim 2 wherein each alkaloid is selected from the group consisting of dihydroquinidine, dihydroquinine, quinidine and quinine.

4. The method of claim 3 wherein the planar aromatic hydrocarbon or nitrogen containing heterocyclic spacer group is a nitrogen heterocyclic.

5. The method of claim 4 wherein said nitrogen heterocyclic is either pyridazine or phthalazine.

6. The method of claim 5 wherein said chiral auxiliary is selected from the group consisting of
   1,4-bis-(9'-O-dihydroquinidyl)-phthalazine,
   1,4-bis-(9'-O-quinidyl)-phthalazine,
   3-6-bis-(9'-O-dihydroquinidyl)-pyridazine,
   3-6-bis-(9'-O-quinidyl)-pyridazine,
   1,4-bis-(9'-O-dihydroquinyl)-phthalazine,
   1,4-bis-(9'-O-quinyl)-phthalazine,
   3,6-bis-(9'-O-dihydroquinyl)-pyridazine and
   3,6-bis-(9'-O-quinyl)-pyridazine.

7. An osmium catalyzed method of producing an asymmetrically dihydroxylated olefin comprising:
   a) combining a chiral auxiliary, an organic solvent, an aqueous solution, a base, a ferricyanide salt and an osmium-containing catalyst in a catalytic quantity, wherein the chiral auxiliary is a cinchona alkaloid covalently linked to an organic substituent of at least 300 daltons molecular weight through a planar aromatic hydrocarbon or nitrogen containing heterocyclic spacer group.
   b) adding the olefin; and
   c) maintaining the resulting combination under conditions appropriate for asymmetric dihydroxylation of the olefin to occur.

8. The method of claim 7 wherein said organic substituent is an alkaloid and said planar aromatic hydrocarbon or nitrogen containing heterocyclic spacer group is a nitrogen heterocyclic.

9. The method of claim 8 wherein each alkaloid is selected from the group consisting of dihydroquinidine, dihydroquinine, quinidine and quinine and said nitrogen heterocyclic is either pyridazine or phthalazine.

* * * * *

UNITED STATES PATENT AND TRADEMARK OFFICE
CERTIFICATE OF CORRECTION

PATENT NO. : 5,260,461
DATED : November 9, 1993
INVENTOR(S) : Jens Hartung and K. Barry Sharpless It is certified that error appears in the above-indentified patent and that said Letters Patent is hereby corrected as shown below:

Column 1, line 6, before the subheading "Related Applications" the following subheading and sentences should be inserted:

---<u>Government Support</u>

This invention was made with government support under Grant No. NIH-R01-GM-28384 by the National Institutes of Health. The government has certain rights in the invention.---

Signed and Sealed this

Thirteenth Day of September, 1994

Attest:

BRUCE LEHMAN

*Attesting Officer*     *Commissioner of Patents and Trademarks*